United States Patent
Takahashi et al.

(10) Patent No.: US 9,498,210 B2
(45) Date of Patent: Nov. 22, 2016

(54) PUNCTURE APPARATUS

(71) Applicant: TERUMO KABUSHIKI KAISHA, Tokyo (JP)

(72) Inventors: Yuusuke Takahashi, Hadano (JP); Masakatsu Kawaura, Sunnyvale, CA (US); Nao Yokoi, Sunnyvale, CA (US)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 291 days.

(21) Appl. No.: 14/222,948

(22) Filed: Mar. 24, 2014

(65) Prior Publication Data

US 2015/0265311 A1   Sep. 24, 2015

(51) Int. Cl.
| | |
|---|---|
| *A61F 2/00* | (2006.01) |
| *A61B 17/062* | (2006.01) |
| *A61B 17/06* | (2006.01) |
| *A61B 17/00* | (2006.01) |
| *A61B 17/34* | (2006.01) |

(52) U.S. Cl.
CPC ....... *A61B 17/062* (2013.01); *A61B 17/06066* (2013.01); *A61B 2017/00805* (2013.01); *A61B 2017/0608* (2013.01); *A61B 2017/3405* (2013.01)

(58) Field of Classification Search
CPC .............. A61B 17/42; A61B 17/0482; A61B 17/06109; A61B 17/062; A61B 17/3468

USPC ........ 600/29–32, 37; 606/167, 170–172, 185
See application file for complete search history.

(56) References Cited

U.S. PATENT DOCUMENTS

| | | | |
|---|---|---|---|
| 6,911,003 B2 | 6/2005 | Anderson et al. | |
| 7,131,943 B2 | 11/2006 | Kammerer | |
| 9,011,475 B1* | 4/2015 | Yokoi | A61B 17/3468 606/185 |
| 9,017,357 B1* | 4/2015 | Kawaura | A61B 17/42 606/185 |

* cited by examiner

*Primary Examiner* — John Lacyk
(74) *Attorney, Agent, or Firm* — Buchanan Ingersoll & Rooney PC

(57) ABSTRACT

A puncture apparatus includes a puncture member rotatable about a rotation center and having a needle tip which rotates together with the puncture member and is configured to puncture living body tissue. The puncture apparatus is also provided with at least one of: i) a vaginal-insertion member insertable into a vagina of a living body and including a vacuum area connected to a suction port; and ii) a urethra insertion member insertable into a urethra of the living body and including a vacuum area connected to a suction port. A cover covers the vacuum area so that the vacuum area does not contact and damage a vaginal wall of the vagina. The cover is movable relative to the vacuum area to expose the vacuum area.

15 Claims, 26 Drawing Sheets

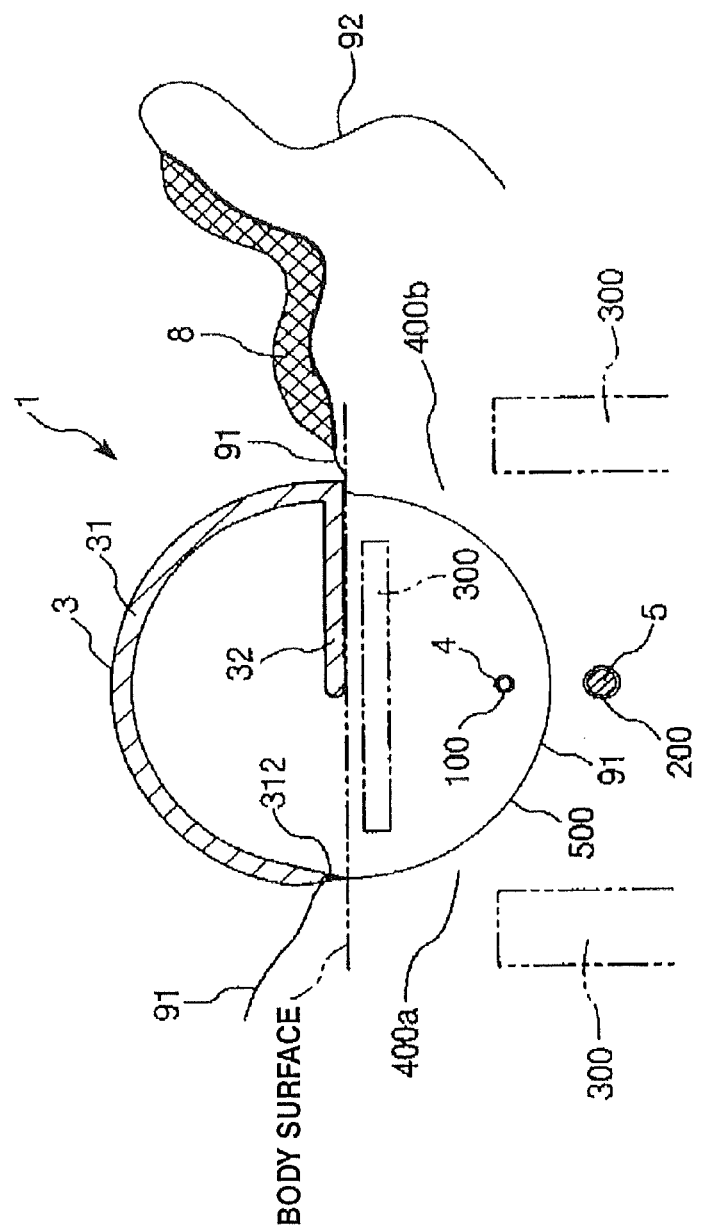

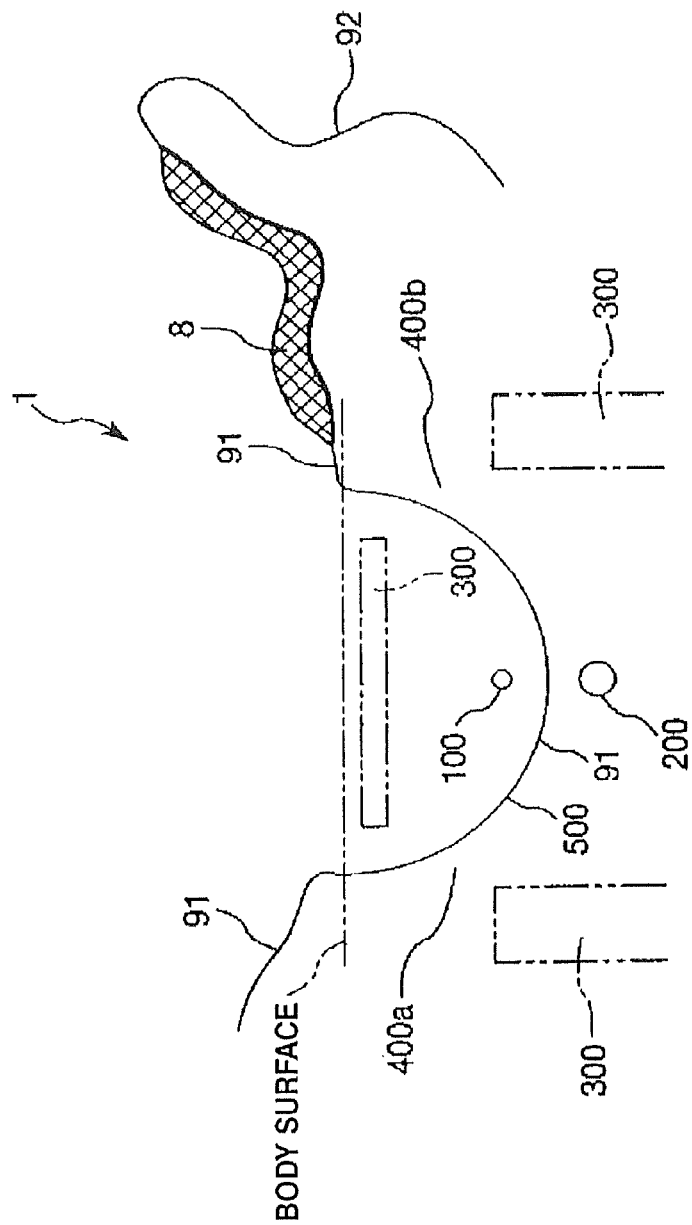

← 16B, 16C

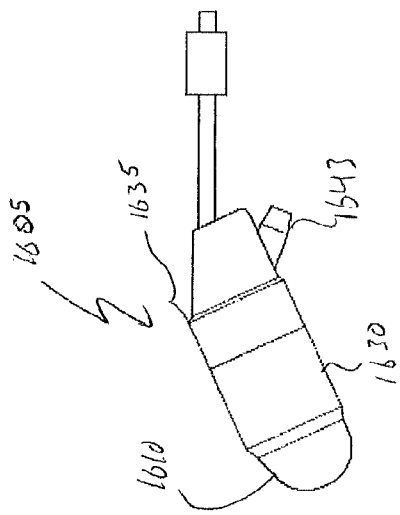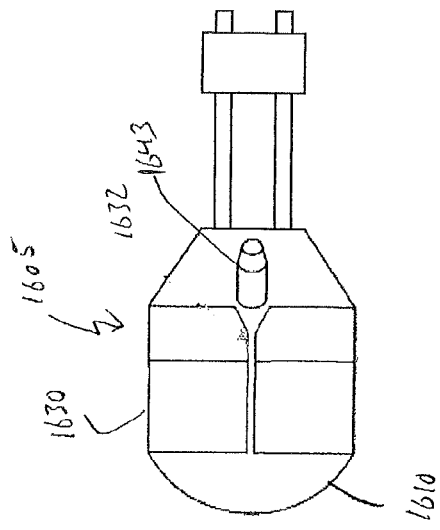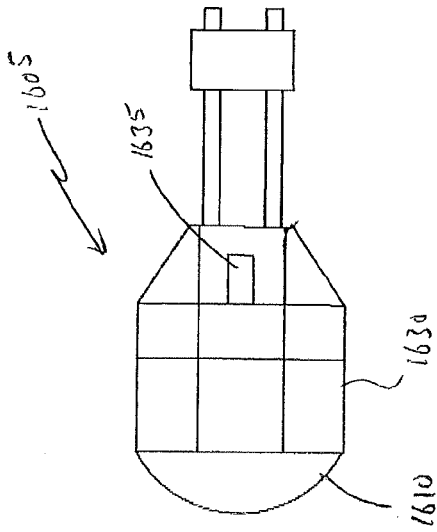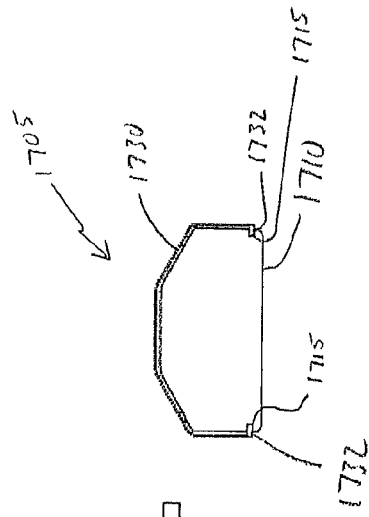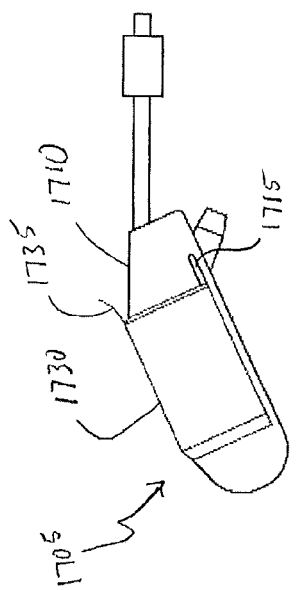

PUNCTURE APPARATUS

CROSS REFERENCES TO RELATED APPLICATIONS

This application contains subject matter disclosed in U.S. Application Publication No. 2013/0253531 published on Sep. 26, 2013, the entire content of which is incorporated herein by reference.

TECHNOLOGICAL FIELD

The present invention generally relates to a puncture apparatus, including a cover used to cover one or more parts of the apparatus to facilitate insertion of the part during insertion into a part of a living body.

BACKGROUND DISCUSSION

When suffering from a urinary incontinence, in particular, when suffering from a stress urinary incontinence, urine leakage occurs caused by the fact that abdominal pressure is applied during a normal exercise or is applied by laughing, coughing, sneezing and the like. For this reason, it is possible to cite, for example, a fact that the pelvic floor muscle which is a muscle for supporting the urethra will loosen caused by a child-bearing or the like.

For the treatment of urinary incontinence, a surgical treatment is effective, in which there is used, for example, a tape-shaped implant referred to as "sling". The "sling" is implanted into the body and the urethra is supported by that sling. An example of this is disclosed in U.S. Pat. No. 6,911,003. In order to indwell the sling inside the body, an operator incises the vagina with a surgical knife, dissects a region between the urethra and the vagina, and communicates that exfoliated region and the outside through an obturator foramen by using a puncture needle or the like. Then, in such a state, the sling is implanted into the body.

However, if the vagina is once incised, there is a fear that there occurs a phenomenon in which the sling will be exposed to the inside of the vagina from a wound caused by the incision thereof, and there is a fear that complications may occur which are caused by an infection from the wound or the like. In addition, since the vagina is incised, the invasiveness of the procedure is rather great and the burden on the patient is large. In addition, there is a fear that the urethra or the like will be damaged in the course of the procedure by the operator, and also, there is a fear that the operator himself will damage his finger tip.

Also, like urinary incontinence, there exists a pelvic organ prolapse as another disorder from which a woman suffers. This disorder is a disorder in which a pelvic organ such as a uterus, a bladder or the like supported in a hammock shape by a pelvic floor muscle group is prolapsed from the vagina caused by the weakening of the pelvic floor muscle group, which can be caused by old age or the like and this is referred to also as a so-called hysterocele or as a cystocele or a rectocele. A repairing method for this pelvic organ prolapse has, in the past, involved a vaginal-wall shortening surgery (colporrhaphy) in which the vaginal wall was incised and the loosened tissue existing between the prolapsed organ and the vaginal wall is partially removed, sutured and shortened. But in recent years, as an alternative technology for that surgery, there has been employed a TVM (Tension-free Vaginal Mesh) surgery and it became possible to prevent the deviation of the pelvic organ from the vagina with lower invasion and also effectively by supporting the prolapsed organ in a hammock shape with a polypropylene-made mesh. An example of this alternative is described in U.S. Pat. No. 7,131,943.

However, like in the treatment of urinary incontinence, when the vagina is incised and the mesh is indwelled, there is a fear that there occurs a phenomenon in which the sling will be exposed to the inside of the vagina from a wound caused by the incision thereof, and there is a fear that there occur complications which are to be caused by an infection from the wound or the like. In addition, since the vagina is incised, the invasiveness of the procedure is rather significant, and the burden on the patient is large. In addition, there is a fear that the urethra or the like will be damaged in the course of the procedure by the operator, and also, there is a fear that the operator himself will damage his finger tip.

SUMMARY

According to one aspect, a puncture apparatus includes: a supporting member and a puncture member rotatably mounted on the supporting member to rotate about a rotation center, with at least a portion of the rotatable puncture member being bent or curved, the distal end portion of the puncture member constituting a needle tip which rotates together with the puncture member and is configured to puncture living body tissue as the puncture member is rotated about the rotation center. The puncture apparatus also includes at least one of: i) a vaginal-insertion member mounted on the supporting member, insertable into a vagina of a living body and including a vacuum area connected to a suction port which is configured to be communicated with a suction source to create a vacuum in the vacuum area of the vaginal-insertion member; and ii) a urethra insertion member mounted on the supporting member, insertable into a urethra of the living body and including a vacuum area connected to a suction port which is configured to be communicated with a suction source to create a vacuum in the vacuum area of the urethra insertion member. A cover covers the vacuum area so that the vacuum area does not contact and damage a vaginal wall of the vagina, and the cover is movable relative to the vacuum area to expose the vacuum area.

According to another aspect, a vaginal-insertion assembly comprises a vaginal-insertion member configured and sized to be inserted into a vagina of a living body, with the vaginal-insertion member including a vacuum area connected to a suction port which is configured to be communicated with a suction source to create a vacuum in the vacuum area of the vaginal-insertion member to draw a vaginal wall of the vagina toward the vacuum area when the vaginal-insertion member in positioned in the vagina. A cover covers the vacuum area so that the vacuum area does not contact and damage a vaginal wall of the vagina when the vaginal-insertion member is inserted into the vagina, and the cover is movable relative to the vaginal-insertion member to expose the vacuum area after the vaginal-insertion member is positioned in the vagina.

Another aspect of the disclosure here involves a urethral insertion assembly comprising a urethral insertion member configured and sized to be inserted into a urethra of a living body, wherein the urethral insertion member includes a vacuum area connected to a suction port which is configured to be communicated with a suction source to create a vacuum in the vacuum area of the urethral insertion member to draw a urethral wall of the urethra toward the vacuum area when the urethral insertion member in positioned in the urethra. The urethral insertion assembly also includes a cover covering the vacuum area so that the vacuum area does not contact and damage a vaginal wall of the urethra when the urethral insertion member is inserted into the urethra, wherein the cover is movable relative to the urethral insertion member to expose the vacuum area after the urethral insertion member is positioned in the urethra.

BRIEF DESCRIPTION OF THE DRAWINGS

FIG. 8 is a cross-sectional view explaining an operating procedure of the puncture apparatus shown in FIG. 1.

FIG. 9 is a cross-sectional view explaining an operating procedure of the puncture apparatus shown in FIG. 1.

FIG. 30 is a top view of the vaginal-insertion assembly forming a part of the disclosed puncture apparatus according to another embodiment disclosed here by way of example.

FIG. 31 is a bottom view of the vaginal-insertion assembly shown in FIG. 58.

FIG. 32 is a side view of the vaginal-insertion assembly shown in FIG. 58.

FIG. 33 is a side view of a vaginal-insertion assembly according to another embodiment disclosed here by way of example.

FIG. 34 is an end view of the vaginal-insertion member shown in FIG. 33.

DETAILED DESCRIPTION

FIGS. 1-11 illustrate features and operational aspects of an embodiment of the puncture apparatus disclosed here. In FIG. 4B, FIG. 5B, FIG. 6B, FIG. 7B and FIGS. 8-11, the oblique lines for the living body are omitted so as to be more easily viewable. In the description which follows, the left side in FIG. 1, FIG. 3, FIG. 4A, FIG. 5A, FIG. 6A, FIG. 7A is the "distal end" and the right side is the "proximal end".

The puncture apparatus 1 shown in these drawings is an apparatus to be used for the treatment of woman's urinary incontinence. That is, it is to be used when burying an implant (tool implanted into a living body) for the treatment of urinary incontinence inside the living body.

The implant is a buriable tool for the treatment of woman's urinary incontinence, that is, a tool for supporting the urethra and a tool for supporting the urethra thereof so as to pull it to the direction separated from the vaginal wall when, for example, the urethra is going to move to the vaginal-wall side. For this implant, it is possible to use, for example, a long object having flexibility.

Figure 7A:
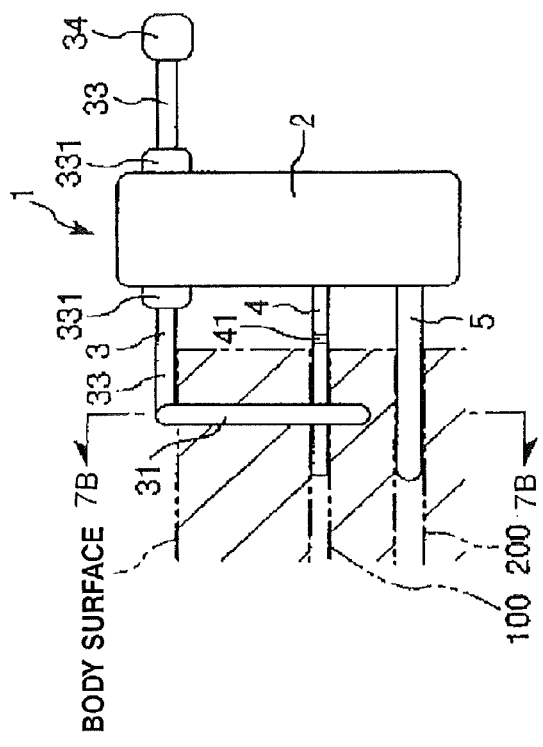
FIGS. 7A and 7B are views explaining an operating procedure of the puncture apparatus shown in FIG. 1, with FIG. 7B taken along the section line 7B-7B in FIG. 7A.
Figure 7B:
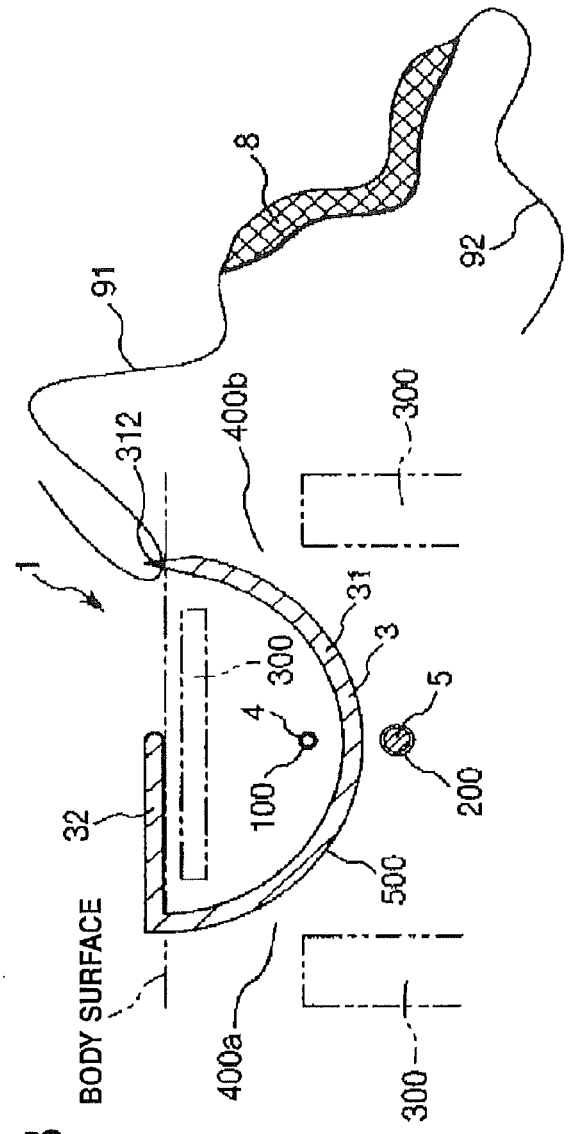

As shown in FIG. 7B, in this embodiment disclosed by way of example, an implant 8 forms an elongated bogy having a mesh-like shape (mesh-shaped) and the overall shape of the implant is a belt-like shape. This implant 8 is referred to as a "sling". It is possible for the implant 8 to be configured as an implant braided in a mesh-like shape (lattice shape), for example, by intersecting line shaped bodies, that is, to be constituted by a braided body having a mesh-like shape. For the line shaped body, examples include a body whose cross-sectional shape is a round shape; whose cross-sectional shape is a flattened shaped, that is, a belt-like shape (ribbon shape); or the like. In addition, at the one end portion of the implant 8, one end portion of a string 91 is fixed and at the other end portion thereof, one end portion of a string 92 is fixed.

Also, there is no limitation in particular for the material forming the implant 8, and it is possible to use, for example, various kinds of resin materials and the like which are biocompatible Also, there is no limitation in particular for the materials forming the strings 91, 92, and it is possible to use, for example, various kinds of resin materials, fibers and the like.

The shape of the implant 8 is not limited to the above-described mesh-like shape.

Figure 1:
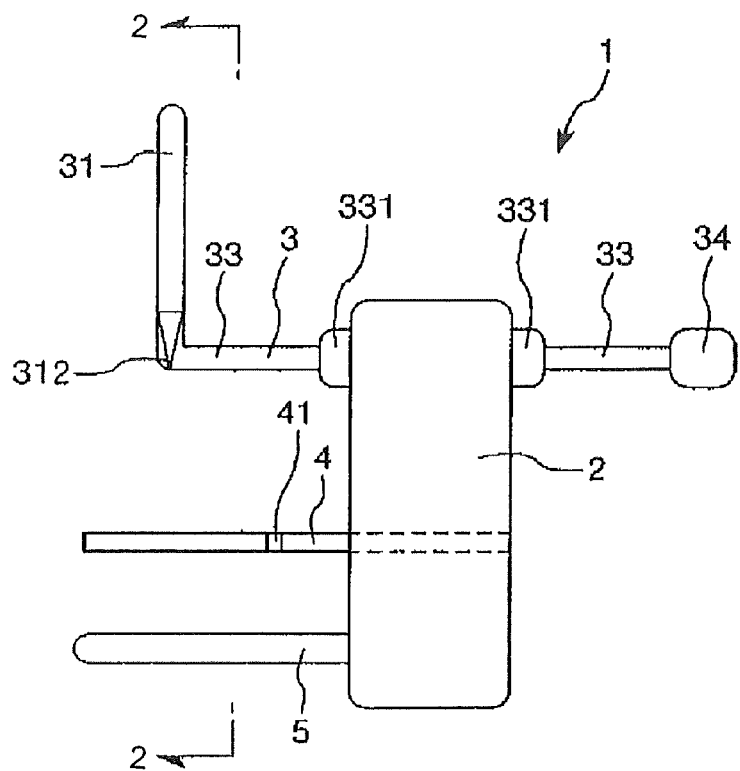
FIG. 1 is a side view of a first embodiment, disclosed by way of example, of a puncture apparatus disclosed here.
Figure 2:
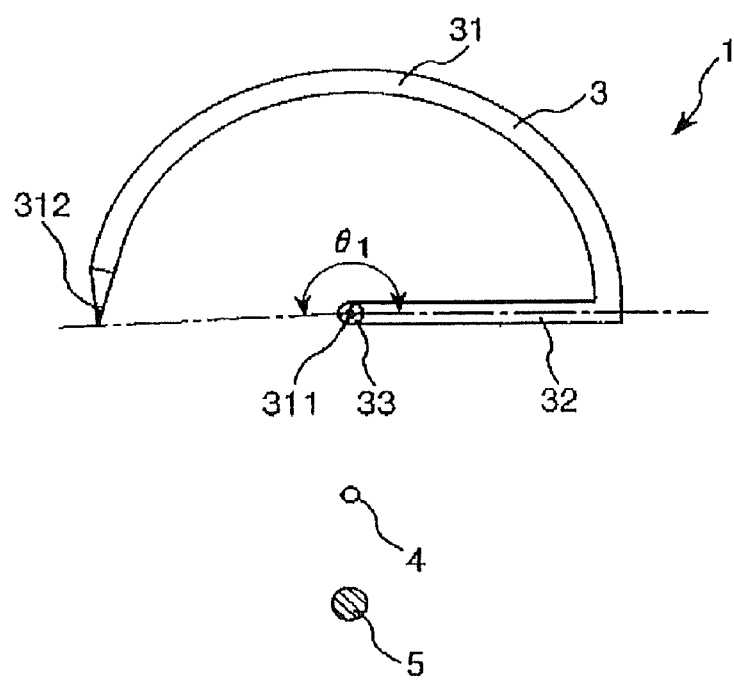
FIG. 2 is a cross-sectional view along the section line 2-2 in FIG. 1.

As shown in FIG. 1 and FIG. 2, the puncture apparatus 1 includes a puncture member 3, a urethral-insertion member 4 possessing an elongated shape and sized and configured to be inserted into a urethra, a vaginal-insertion member 5 possessing an elongated shape and sized and configured to be inserted into a vagina; and a supporting member 2 for supporting the puncture member 3, the urethral-insertion member 4 and the vaginal-insertion member 5. The supporting member 2 is an example of a restriction means for restricting the positional relationship between the puncture member 3 and the urethral-insertion member 4 (and also the vaginal-insertion member 5, if desired), as will be discussed in more detail below. The puncture member 3 includes a puncture needle 31 at a distal end portion of the puncture member for puncturing living body tissue, an axial portion 33 and an interlock portion 32 connecting the puncture needle 31 and the axial portion 33.

Figure 3:
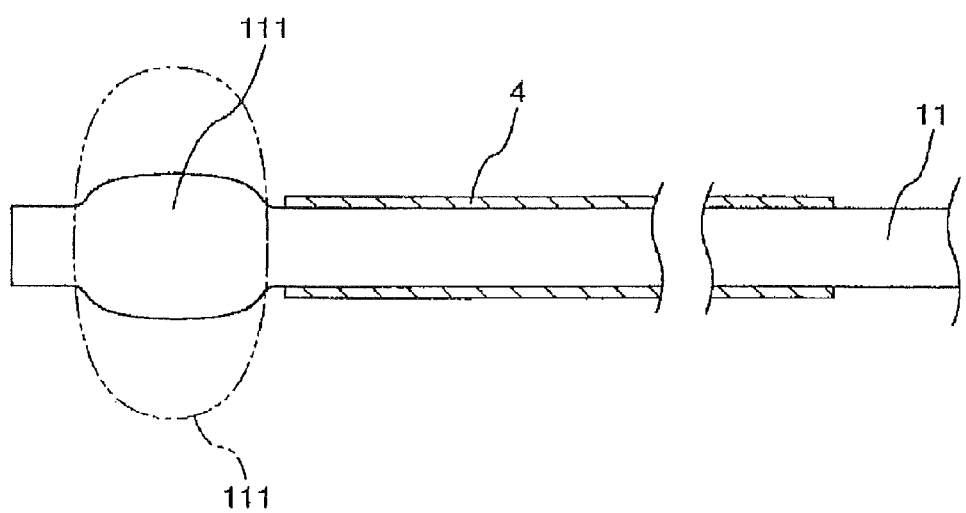
FIG. 3 is a cross-sectional view showing a state in which a balloon catheter is inserted into a urethral-insertion member of the puncture apparatus shown in FIG. 1.

In this embodiment, the urethral-insertion member 4 is firmly-fixed to the supporting member 2. This urethral-insertion member 4 is a straight tubular-shaped body composed of a non-elastic rigid material, and has an opening at the proximal end that opens to the proximal surface of the supporting member 2. It is possible to insert into the inside of the urethral-insertion member 4 various kinds of long-shaped (elongated) medical tools such as, for example, a balloon catheter 11, which is provided with an expandable and contractible balloon 111 at its distal portion such as shown in FIG. 3. In FIG. 3, a state in which the balloon 111 is contracted is indicated by a solid line and a state in which the balloon 111 is expanded is indicated by a two-dot chain line.

The balloon 111 of this balloon catheter 11 functions as a restriction structure for restricting the position of the urethral-insertion member 4 in the axis direction (longitudinal direction) inside the urethra. More specifically, when using the puncture apparatus 1, the balloon 111 is inserted into a bladder of a patient, the positional relation in the axial direction between the balloon catheter 11 and the urethral-insertion member 4 is fixed, and also, by a mechanism in which the balloon 111 is hooked onto the bladder neck in a state of being expanded, the position of the urethral-insertion member 4 with respect to the bladder and the urethra is fixed.

A balloon expanding tool such as, for example, a syringe is connected to a port which communicates with a lumen in communication with the balloon 111 of the balloon catheter 11. The expansion and contraction of the balloon 111 is carried out by feeding an operating fluid supplied by that balloon expanding tool into the inside of the balloon 111 through the mentioned lumen or by pulling out the operating fluid. As the operating fluid for the expansion of the balloon, it is possible to use, for example, a liquid such as a physiological saline or the like, a gas, and the like.

Also, it is possible to use the balloon catheter 11 for the urination of the patient when using the puncture apparatus 1.

A marker 41 is also provided at the outer circumferential portion of the urethral-insertion member 4. This marker 41 is arranged such that the marker 41 is positioned at the urethral opening when the urethral-insertion member 4 is inserted into the urethra and the distal portion of the urethral-insertion member 4 is positioned just before the bladder.

In this embodiment, the vaginal-insertion member 5 is firmly-fixed to the supporting member 2. This vaginal-insertion member 5 is a straight bar shape. Also, the distal portion of the vaginal-insertion member 5 is rounded. Thus, it is possible to insert the vaginal-insertion member 5 smoothly into the vagina.

Also, the vaginal-insertion member 5 is arranged on the lower side of the urethral-insertion member 4 and is separated or spaced from the urethral-insertion member 4 by a predetermined distance such that the axis of the vaginal-insertion member 5 and the axis of the urethral-insertion member 4 are parallel. Preferably at least a proximal portion of the vaginal-insertion member 5 may be parallel with a proximal portion of the urethral-insertion member 4.

There is no limitation in particular for the materials forming the vaginal-insertion member 5, the urethral-insertion member 4 and the supporting member 2. It is possible to use, for example, various kinds of resin materials or the like, or various kind of metal materials or the like.

With regard to the puncture member 3, the axial portion 33 of the puncture member, also constituting the rotational axis of the puncture member, is placed (mounted) in a freely rotatable manner on the supporting member 2.

Also, the axial portion 33 is arranged on the upper side of the urethral-insertion member 4 and is separated or spaced from the urethral-insertion member 4 by a predetermined distance such that the axis of the axial portion 33 and the axis of the urethral-insertion member 4 are parallel. Also, when seen from the axial direction of the axial portion 33, the axial portion 33, the urethral-insertion member 4 and the vaginal-insertion member 5 are arranged on a straight line. The axis of the axial portion 33 exists in the same plane (plane surface) as that of the axis of the urethral-insertion member 4. The axis of the axial portion 33 also exists on the same plane (plane surface) same as that of the axis of the vaginal insertion member 5. Thus, as seen in FIG. 2, the axis of the axial portion 33, the axis of the urethral-insertion member 4, and the axis of the vaginal insertion member 5 lie in a common plane (a plane perpendicular to the plane of the paper).

This axial portion 33 passes completely through the supporting member 2 in the right and left direction in FIG. 1. On the distal side and the proximal side of the axial portion 33, there are formed a flange 331 and a flange 332 respectively through the supporting member 2, and depending on these flanges 331, 332, the movement toward the axis direction of the axial portion 33 with respect to the supporting member 2 is blocked.

The distal end of the puncture needle 31 has a sharp needle tip, and the puncture needle 31 bends in an arc shape centered on the axial portion 33. Also, in FIG. 1, the axis of the puncture needle 31 and the axis of the axial portion 33 are orthogonal. Thus, when the puncture member 3 is moved rotationally, the needle tip of the puncture needle 31 moves along the arc in a surface perpendicular to the axis of the axial portion 33 and more specifically, moves in a surface in which the aforesaid axis is a normal line.

The puncture needle 31 moves along a predetermined orbit. It is possible for the needle tip of the puncture needle 31 to move by drawing a preliminarily defined arc-shaped orbit centered on the axial portion 33. The orbit of the puncture needle 31 passes a far-position side compared with the urethral-insertion member 4. The orbit of the puncture needle 31 passes a portion between the urethral-insertion member 4 and vaginal-insertion member 5.

There is no problem even if the distal end of the puncture needle 31 has an obtuse needle tip of such a degree in which there is no obstacle to progress toward the inside of the living body tissue. It is possible to employ another or different member for the needle tip of the puncture needle 31.

Also, in this embodiment disclosed by way of example, the needle tip of the puncture needle 31 is directed toward the counterclockwise direction in FIG. 2, but it is not limited to this configuration as it is also possible for the needle to be directed toward the clockwise direction in FIG. 2.

It is also possible for the puncture needle 31 to be solid and it is also possible for the needle to have a tubular and hollow shape.

Also, in this embodiment, the puncture needle 31 is arranged on the proximal side relative to the distal portion (distal-most end) of the urethral-insertion member 4 in the axial direction of the urethral-insertion member 4.

It is also possible however for the puncture needle 31 to be arranged at the same position as the distal portion (distal-most end) of the urethral-insertion member 4 in the axial direction of the urethral-insertion member 4. Additionally, the needle 32 can be arranged on the distal side of the distal portion (distal-most end) of the urethral-insertion member 4.

Here, the supporting member 2 restricts the positional relation between the puncture member 3 and the urethral-insertion member 4 such that when the puncture member 3 moves rotationally (rotates) and punctures the living body tissue, the needle tip of the puncture needle 31 passes, relative to the urethral-insertion member 4 or an extended line (imaginary continuation) of such member, a far-position side from the center 311 of the puncture needle 31 so that is passes to a lower side of the urethral-insertion member 4 or an extended line of such member. That is, during rotation of the needle 31, the tip of the needle passes on the side (lower side in FIG. 2) of the urethral-insertion member 4 that is opposite the rotation center 33 of the needle such that the urethral-insertion member 4 is positioned between the center 33 and the lower portion of the path of movement of the needle tip. The center 311 of the puncture needle 31 is the center of the arc in the puncture needle 31, that is, is the rotary center of the puncture needle 31 (puncture member 3).

The positional relationship between the puncture member 3 and the urethral-insertion member 4 is fixed such that the orbit of the needle tip of the puncture member 3 does not intersect the urethral-insertion member 4 or the extended line thereof and such that the orbit of the needle tip of the puncture needle 31 will pass the lower side of the urethral-insertion member 4 or the extended line (imaginary extension) of such line.

With regard to the positional relation between the orbit of the needle tip of the puncture member 3 and the urethral-insertion member 4, other than the configuration in which the position is maintain by such a member as the aforementioned supporting member 2, it is possible to employ a guide member which is connected with the urethral-insertion member 4 and which is insertable into the urethral-insertion member 4 such that the puncture member 3 makes a movement by a certain orbit. Also, it is possible to employ a configuration in which the urethral-insertion member 4 and the puncture member 3 are connected directly and the puncture member 3 is configured to make a movement by a certain orbit, whereby the positional relation is fixed such that the orbit of the needle tip of the puncture needle 31 will pass the lower side of the urethral-insertion member 4 or the extended line thereof.

Also, it is possible for the urethral-insertion member 4 to be provided with a marker which is visually recognizable under the noninvasive monitoring of the inside of the body by X-ray, ultrasound or the like. While confirming the position of the urethral-insertion member 4 by a monitor while emitting the X-ray or the ultrasound, it is possible to pass the needle tip through a desired position by setting a condition in which the orbit of the needle tip of the puncture needle 31 will surely pass the lower side of the urethra and by executing the puncture. Further, it is possible for the vaginal insertion member 5 to be provided with a similar marker. It is possible to employ a configuration in which the orbit of the needle tip of the puncture needle 31 is displayed on the monitor such that the position of the urethral-insertion member 4 and the position of the orbit can be confirmed on the monitor. In a case in which the position of the urethral-insertion member 4 and the position of the orbit on the monitor intersect each other, a mechanism can be provided which can move the puncture member 3 automatically or manually such that the position of the orbit does not overlap. When employing such an embodiment, the positional relation between the orbit of the needle tip of the puncture needle 31 and the urethral-insertion member 4 can be maintained by a series of systems including the mechanism mentioned above.

Further, the supporting member 2 restricts the positional relation between the puncture member 3 and the vaginal-insertion member 5 such that when the puncture member 3 moves rotationally and punctures the living body tissue, the needle tip of the puncture needle 31 does not interfere with the vaginal-insertion member 5 and the extended line thereof.

More specifically, the supporting member 2 restricts the positional relation between the puncture member 3, the urethral-insertion member 4 and the vaginal-insertion member 5 such that when the puncture member 3 rotates or moves rotationally and punctures the living body tissue, the needle tip of the puncture needle 31 passes a position between the urethral-insertion member 4 or the extended line thereof and the vaginal-insertion member 5 or the extended line thereof.

Thus, depending on the puncture needle 31, it is possible to puncture the living body tissue by avoiding the urethra and the vaginal wall, and it is possible to prevent a phenomenon in which the puncture needle 31 will puncture the urethra and will puncture the vaginal wall.

Also, the orbit of the needle tip of the puncture needle 31 is determined so that it is possible for the operator himself to prevent a phenomenon of puncturing his finger tip by the puncture needle 31. Safety can thus be obtained.

There is no limitation in particular for the center angle θ1 of the arc of the puncture needle 31. This angle is an angle to be set arbitrarily in response to various conditions, and this angle is set such that when puncturing living body tissue by the puncture needle 31, it becomes possible for the puncture needle 31 to enter into the body from one body surface of the patient, to pass the lower side of the urethra and to protrude to the body outside from the other body surface.

Specifically, it is preferable for the center angle θ1 of the arc of the puncture needle 31 to be 150° to 270°, more preferably 170° to 250° or less, and still more preferably 190° to 230°.

Thus, when puncturing living body tissue by the puncture needle 31, it is possible for the puncture needle 31 to reliably enter into the body from one body surface of the patient, to pass the lower side of the urethra and to protrude to the body outside from the other body surface.

Also, at the distal portion of the puncture needle 31, there is formed a through-hole 312. This through-hole 312 passes through the puncture needle 31 toward the direction which is perpendicular with respect to the axis of the puncture needle 31. Also, either one of the strings 91, 92 which are fixed to the aforementioned implant 8 is inserted into this through-hole 312 and is detachably held (see FIG. 7B).

Also, at the proximal portion of the axial portion 33, there is provided a grasping unit 34 as an operation unit for operating the puncture member 3 rotationally. In this embodiment disclosed by way of example, this grasping unit 34 is in the shape of a rectangular solid. When moving the puncture member 3 rotationally, the grasping unit 34 is grasped by hand and fingers, and is moved rotationally toward a predetermined direction. Needless to say, the shape of the grasping unit 34 is not limited by the illustrated and described configuration.

There is no limitation in particular for the material forming the puncture member 3 and it is possible to use various kinds of rigid materials, such as metal materials, such as metal materials and resin materials. Examples of metal materials include stainless steel, aluminum or aluminum alloy and titanium or titanium alloy, or the like, and examples of resin materials include polyimide or polyamide, or the like. Puncture member 3 may include an outer elongate tube and an inner solid shaft.

Set forth next is a description of an operating procedure using the puncture apparatus 1, that is, a procedure when burying the implant 8 inside the living body.

Initially, there will be explained a method of forming a path for burying the implant 8 inside the living body.

Figure 4A:
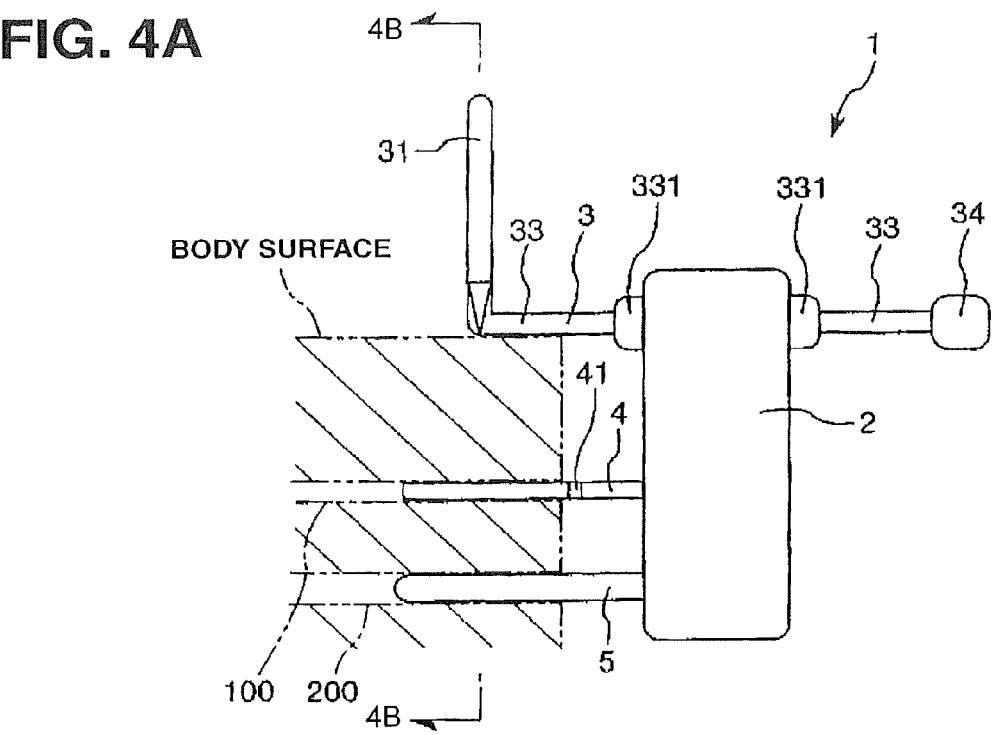
FIGS. 4A and 4B are views explaining an operating procedure of the puncture apparatus shown in FIG. 1, with FIG. 4B taken along the section line 4B-4B in FIG. 4A.
Figure 4B:
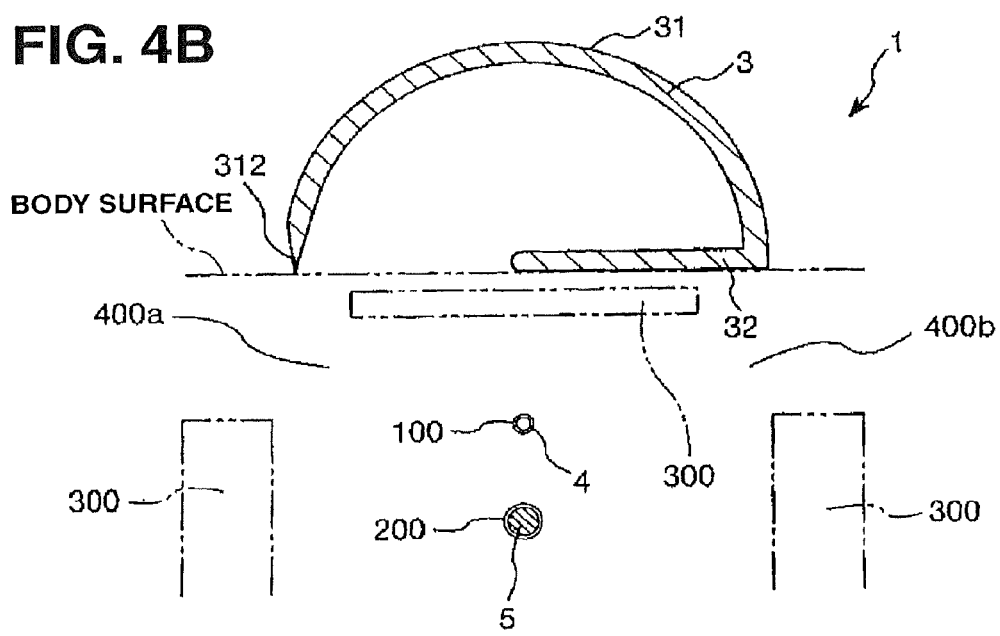

First, as shown in FIGS. 4A and 4B, the puncture apparatus 1 is attached to a patient. More specifically, the urethral-insertion member 4 of the puncture apparatus 1 is inserted into a urethra 100 of the patient and concurrently, the vaginal-insertion member 5 is inserted into a vagina 200 of the patient. At that time, the insertion is carried out such that the marker 41 will be positioned at the urethral orifice or on the front side of the urethral orifice. Thus, it is possible to arrange the distal portion of the urethral-insertion member 4 on the front side of the bladder.

Figure 5A:
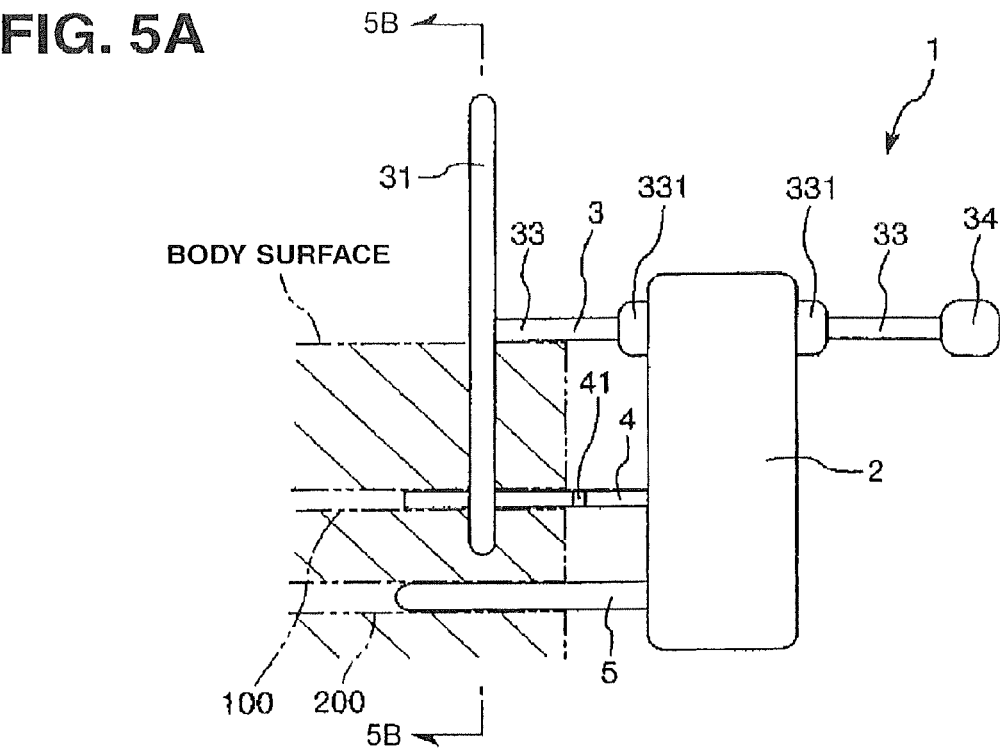
FIGS. 5A and 5B are views explaining an operating procedure of the puncture apparatus shown in FIG. 1, with FIG. 5B taken along the section line 5B-5B in FIG. 5A.
Figure 5B:
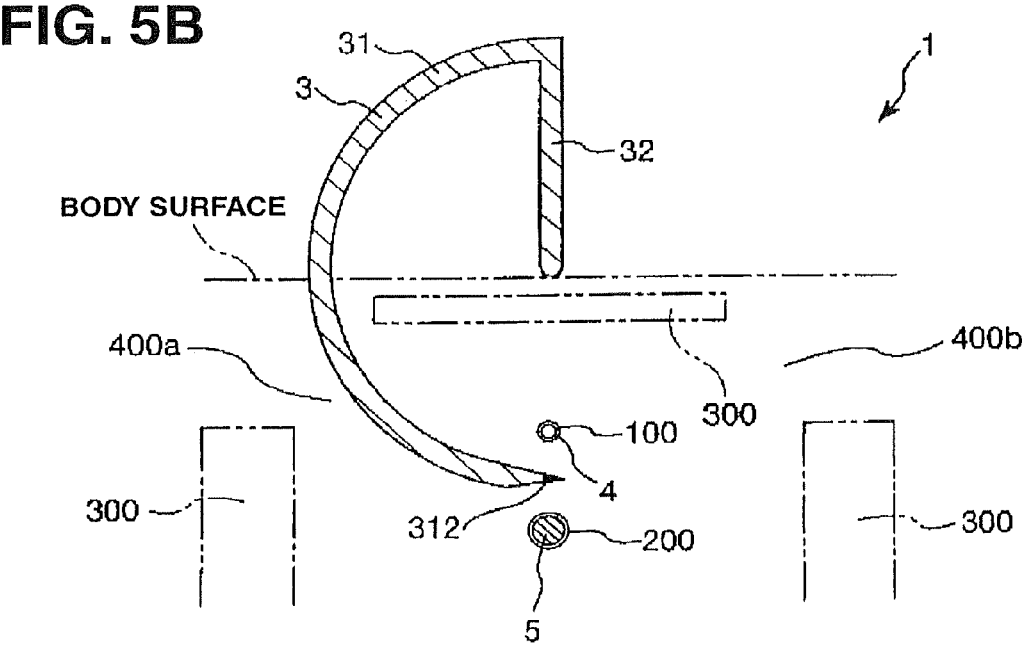
Figure 6A:
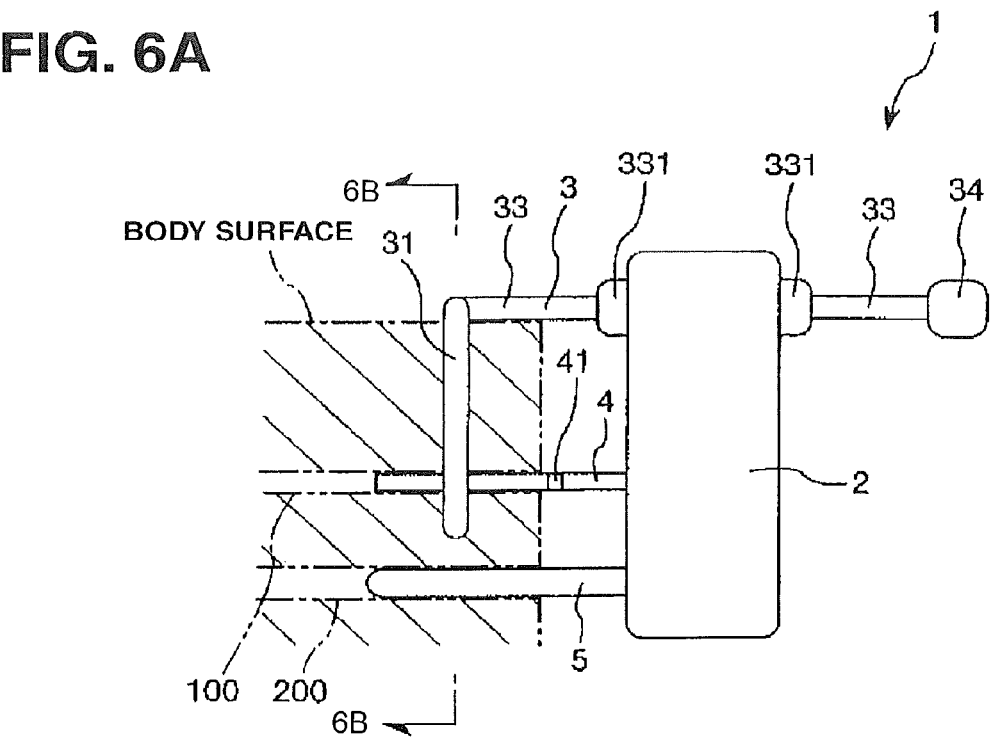
FIGS. 6A and 6B are views explaining an operating procedure of the puncture apparatus shown in FIG. 1, with FIG. 6B taken along the section line 6B-6B in FIG. 6A.
Figure 6B:
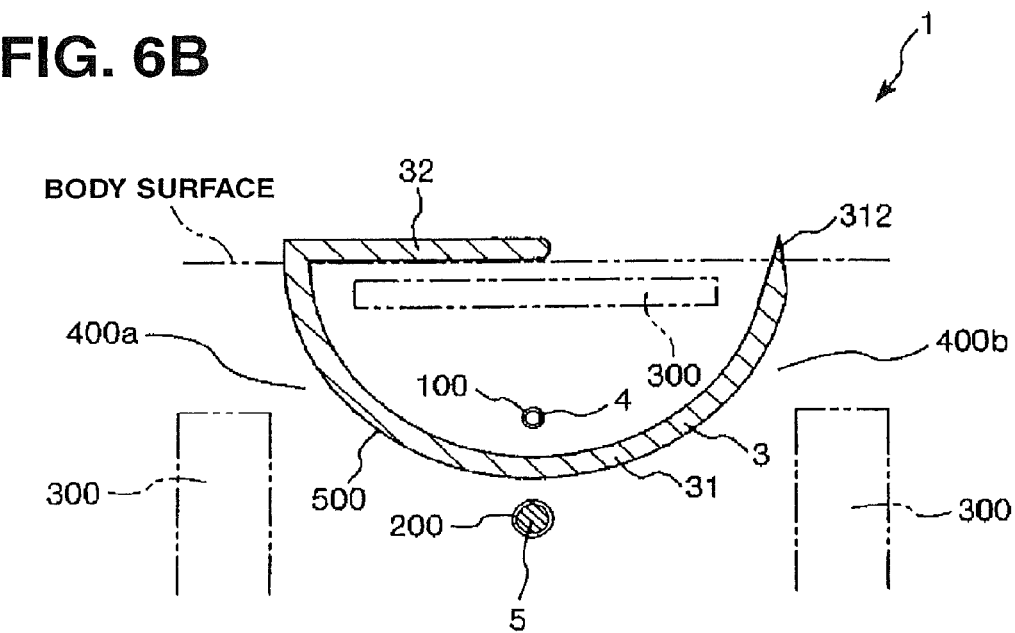

Next, as shown in FIGS. 5A, 5B, 6A and 6B, the grasping unit 34 is grasped and the puncture member 3 is rotated counterclockwise in FIG. 5B and FIG. 6B.

Thus, the member 3 percutaneously moves into a tissue of the body. First the needle tip of the puncture needle 31 moves counterclockwise in FIG. 5B and FIG. 6B along the arc of the needle; punctures the body surface at an interlock region of the patient on the left side in FIG. 5B and FIG. 6B or at a region in the vicinity of such region; enters into the body; passes an obturator foramen 400a of a pelvis 300; passes the lower side of the urethra 100, that is, passes between the urethra 100 and the vagina 200; passes an obturator foramen 400b of the pelvis 300; and protrudes back outside the body by exiting the body surface at an interlock region on the right side in FIG. 5B and FIG. 6B or at a region in the vicinity of such region. Thus, for the patient, there is formed a through-hole 500 which starts from the body surface at an interlock region on the left side in FIG. 5B and FIG. 6B or at a region in the vicinity of such region and which reaches the body surface at an interlock region on the right side in FIG. 5B and FIG. 6B or at a region in the vicinity of such region by passing through the obturator foramen 400a, the space between the urethra 100 and the vagina 200 and the obturator foramen 400b.

The through-hole 500 maintains a non-opened state with respect to the urethra 100 and the vagina 200. It is preferable for the orbit of the needle tip of the puncture needle 31 to pass a region on the inner side (near the pubic-bone connection) from the center of the obturator foramen 400b of the pelvis 300. It is more preferable for the orbit to pass a region referred to as a so-called safety zone (or safety-entry zone) within the regions near the pubic-bone connection from the center of the obturator foramen 400b. This is because there are few nerves or blood vessels in such regions, for which injuries are desired to be avoided, and because it is possible to carry out the puncture safely.

There will next be explained a procedure of passing an implant through the path and indwelling the implant.

As shown in FIGS. 7A and 7B, the end portion of either one of the strings 91, 92 fixed to the implant 8 is inserted through the through-hole 312 of the puncture needle 31, there is inserted the end portion of either one of the strings 91, 92 fixed to the implant 8. In the illustrated example, the end portion of string 91 is inserted through the through-hole 312 of the puncture needle 31. Thus, the end portion of the string 91 is held at the distal portion of the puncture needle 31.

Next, as shown in FIG. 8, the grasping unit 34 is grasped and the puncture member 3 is rotated clockwise in FIG. 8.

Thus, the needle tip of the puncture needle 31 moves clockwise in FIG. 8 along an arc; enters the body from the interlock region of the patient on the right side in FIG. 8 or from a body surface in a region in the vicinity of such region; passes the obturator foramen 400b of the pelvis 300; passes the lower side of the urethra 100, that is, passes between the urethra 100 and the vagina 200; passes the obturator foramen 400a of the pelvis 300; and exits to the outside of the body from the interlock region on the left side in FIG. 8 or from a body surface in a region in the vicinity of such region. More specifically, the puncture needle 31 is pulled out or moved to the outside of the body.

Next, as shown in FIG. 9, the end portion of the string 91 is pulled out from the through-hole 312 of the puncture needle 31. Also, the puncture apparatus 1 is removed from the patient. More specifically, the urethral-insertion member 4 is pulled out from the inside of the urethra 100 and concurrently, the vaginal-insertion member 5 is pulled out from the inside of the vagina 200 of the patient.

Figure 10:
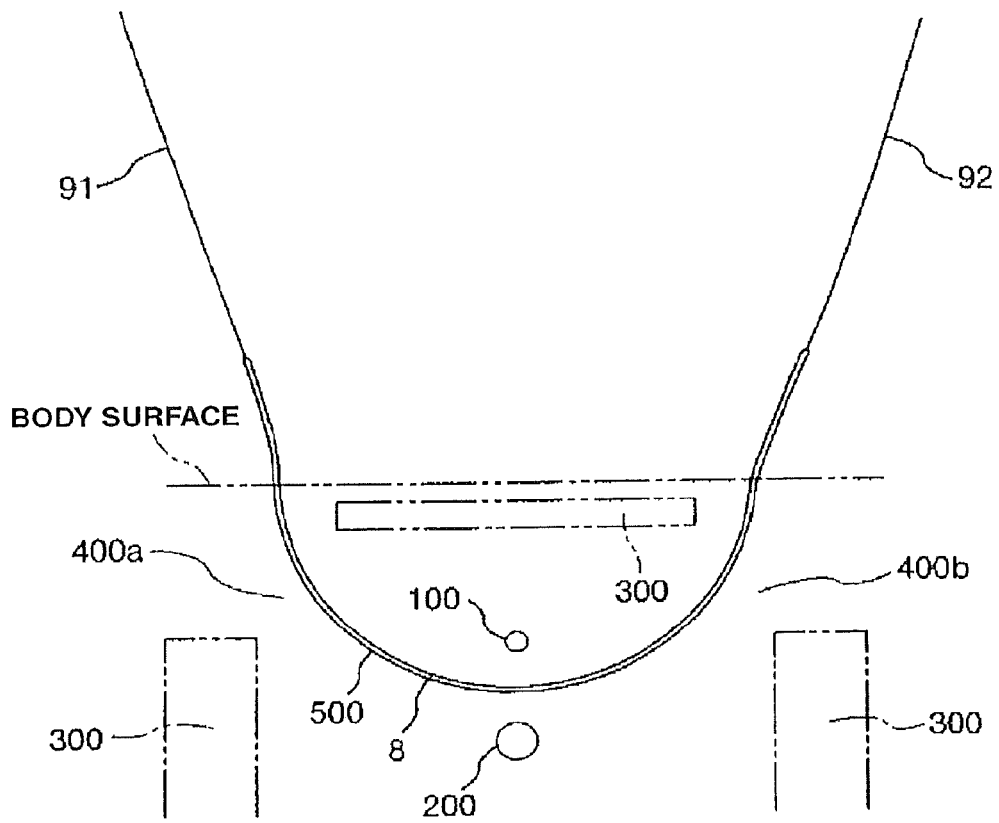
FIG. 10 is a cross-sectional view explaining an operating procedure of the puncture apparatus shown in FIG. 1.

Next, as shown in FIG. 10, the string 91 is pulled while pulling the string 92, the implant 8 is inserted into the through-hole 500 which is formed in the patient; and while the end portion of the implant 8 on the right side in FIG. 10 is remained on the outside of the body, the end portion of the implant 8 on the left side in FIG. 10 is pulled out from the through-hole 500 to the outside of the body.

Figure 11:
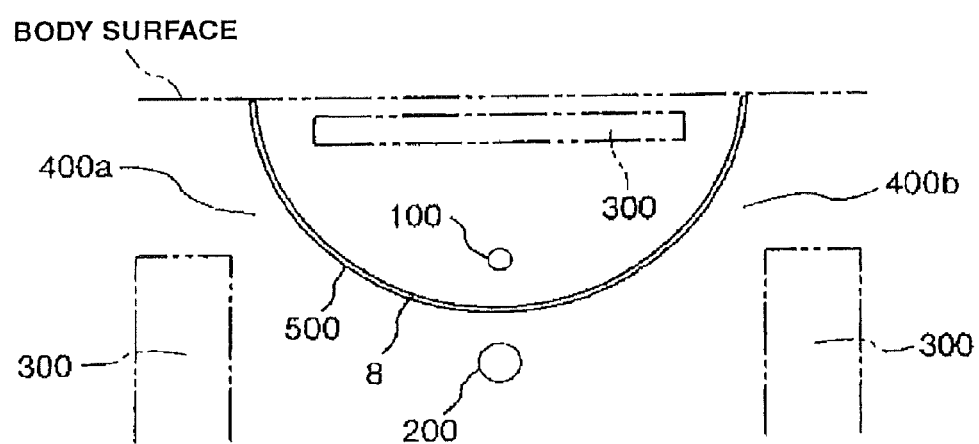
FIG. 11 is a cross-sectional view explaining an operating procedure of the puncture apparatus shown in FIG. 1.

Next, as shown in FIG. 11, the strings 91, 92 are pulled respectively by predetermined forces, the position of the implant 8 with respect to the urethra 100 is adjusted, unnecessary portions of the implant 8 are cut out, and afterward the procedure is completed.

As explained above, according to this puncture apparatus 1, when indwelling an implant, it is possible to make a correspondence only by a procedure exhibiting relatively low invasiveness, involving a puncture of the puncture needle 31 or the like, and it is not necessary to carry out a highly invasive incision or the like, so that the burden on the patient is relatively small and also, the safety of the patient is quite high.

Also, because the living body can be punctured by the puncture needle 31 by avoiding the urethra and the vaginal wall, it is possible to prevent a phenomenon in which the puncture needle 31 will puncture the urethra and will puncture the vaginal wall, thus facilitating a safe result. Also, it is possible for the operator himself to prevent a phenomenon in which his finger tip will be punctured by the puncture needle 31 and so safety can be obtained.

Also, it is possible to prevent a phenomenon in which, such as in a conventional case of incising a vagina, the implant is exposed to the inside of the vagina from a wound caused by the incision and in which complications occur which are caused by an infection from the wound or the like.

In this embodiment disclosed by way of example, the puncture hole formed for the patient by the puncture needle 31 is a through-hole, but it is not limited by this configuration and it is possible for the puncture hole not to employ a passing-through type.

Also, the urethral-insertion member is not limited to a tubular-shaped member and it is possible, for example, to employ a solid member, and in addition, it is also possible to employ a member which is hollow and in which either one or both of the distal portion and the proximal portion of the hollow member are occluded.

The distal portion of the urethral-insertion member can be provided with an expandable a contractible balloon as a restriction structure for restricting the position in the axial direction of the urethral-insertion member inside the urethra.

Also, in this embodiment, the puncture needle of the puncture member is a needle, the whole of which is bent in an arc shape. But the needle is not limited to this shape or configuration, and it is possible, for example, to employ a needle including a region bent in an arc shape only for a portion of the length of the needle. More specifically, it is enough if the puncture needle includes a region bent in an arc shape at least for a portion of the extent of the needle.

Also, it is sufficient if the puncture needle of the puncture member includes a bent region at least for a portion of its length and it is possible, for example, to employ a needle, the whole of which is bent in an elliptical arc shape and to employ a needle which includes a region bent in an elliptical arc shape only for a portion of its length. More specifically, it is possible for the puncture needle to include a region bent in an elliptical arc shape at least for a portion of its extent.

Figure 19A:
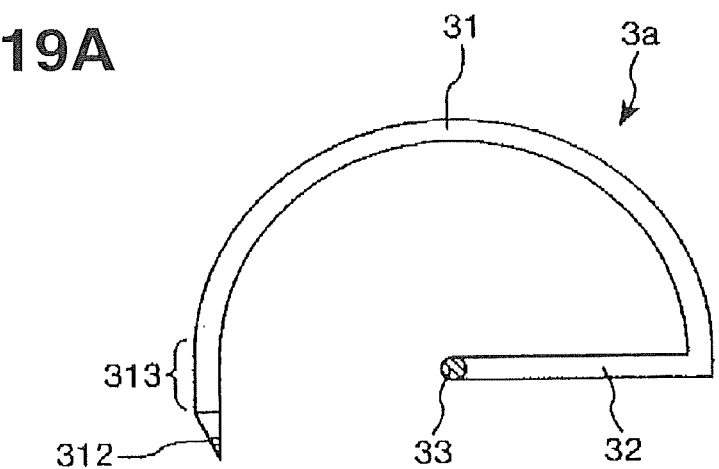
FIGS. 19A to 19C are cross-sectional views showing another example of the puncture member disclosed here.

Set forth next is a description of other examples of the puncture member disclosed here. The puncture needle 31 of the puncture member 3a shown in FIG. 19A includes a linear shaped portion 313 forming a linear shape at the distal portion of the needle. This linear-shaped portion 313 protrudes in the direction of a tangent line of the end portion of the needle from the end portion on the distal side of the arc of the puncture needle 31.

In case of using this puncture member 3a, before rotating the puncture member 3a, the puncture member 3a is first pressed against the patient and the linear shaped portion 313 of the puncture needle 31 punctures the patient.

Figure 19B:
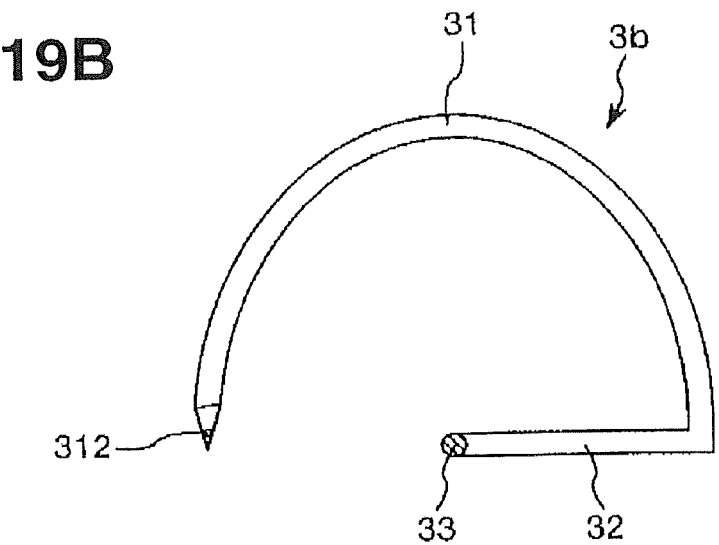

The puncture needle 31 of the puncture member 3b shown in FIG. 19B is bent in an elliptical arc shape centered on the axial portion 33. The long axis direction of the ellipse coincides with the up and down direction in FIG. 19B.

It is possible to use this puncture member 3b preferably in a case in which the urethra of the patient is positioned at a deep place from her body surface.

Figure 19C:
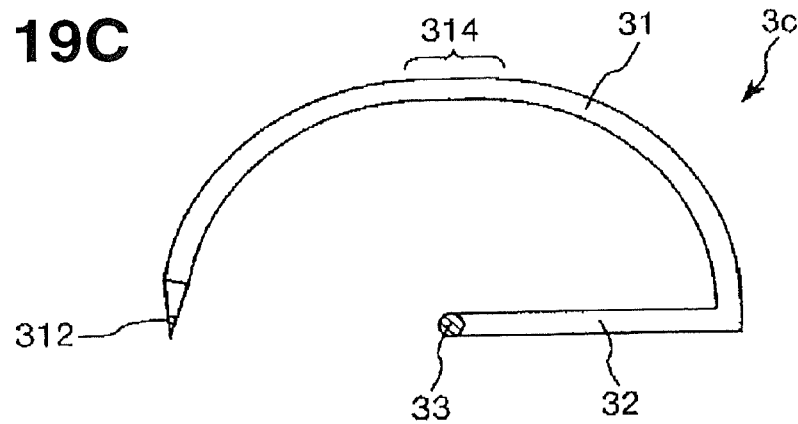

The puncture needle 31 of the puncture member 3c shown in FIG. 19C includes a linear shaped portion 314 forming a linear shape on the midway portion of the needle, that is, at the intermediate portion of the puncture needle 31.

It is possible to use this puncture member 3c preferably in a case in which the urethra of the patient is positioned at a shallow place from her body surface.

Figure 12:
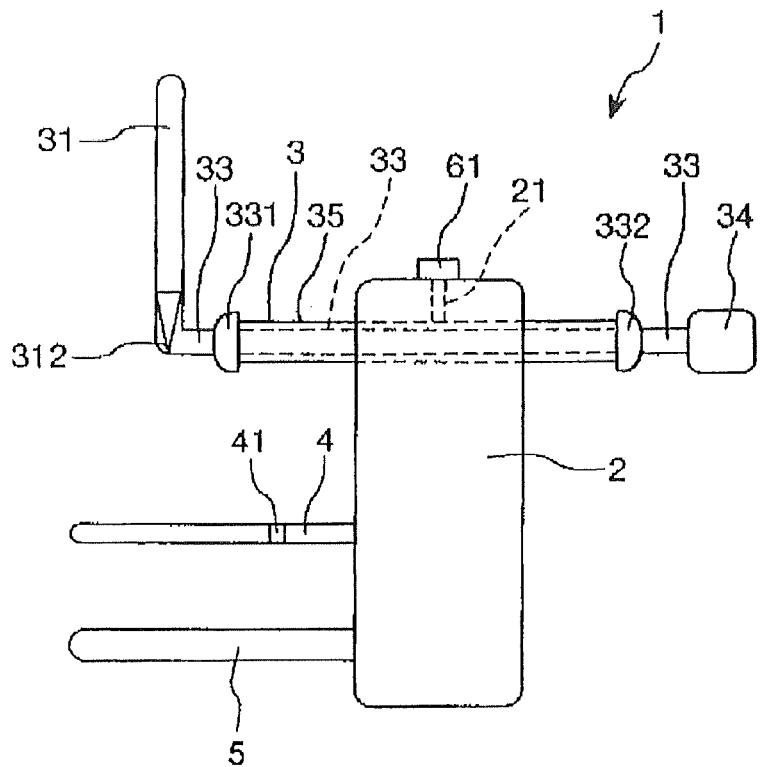
FIG. 12 is a side view of a second embodiment, disclosed by way of example, of a puncture apparatus disclosed here.

FIG. 12 illustrates a second embodiment representing another example of the puncture apparatus disclosed here. The following description of this embodiment will be set forth assuming that the left side in FIG. 12 is the "distal end" and the right side in FIG. 12 is the "proximal end".

The following description of the second embodiment will focus primarily on aspects or features of the puncture apparatus different from those of the first embodiment described above. Features and aspects of this second embodiment of the puncture apparatus that are similar to those described above in the first embodiment are identified by common reference numerals, and a detailed description of such aspects and features is not repeated.

As shown in FIG. 12, in the puncture apparatus 1' of the second embodiment, the axial portion 33 of the puncture member 3 is supported movably by the supporting member 2 in the axial direction of the axial portion 33, that is, in the axial direction of the urethral-insertion member 4.

Specifically, the puncture member 3 includes a tubular body 35 through which an axial portion 33 is inserted and which rotatably supports that axial portion 33. Also, the flanges 331, 332 are arranged on the distal side and on the proximal side of the tubular body 35 respectively, and owing to these flanges 331, 332, the movement in the axial direction of the axial portion 33 with respect to the tubular body 35 is blocked. That is, the flanges 331, 332 permit axial movement of the tubular body 35 relative to the supporting member 2, but limit the amount of such axial movement. The tubular body 35 is placed (mounted) on the supporting member 2 movably in the axial direction of the axial portion 33, that is, in the axial direction of the urethral-insertion member 4.

By moving the puncture member 3 in the axial direction of the urethral-insertion member 4, it is possible for the puncture needle 31 to be disposed in the axial direction of the urethral-insertion member 4 at any position, including on the proximal side of the distal-most tip of the urethral-insertion member 4, at the same position as that of the distal-most tip of the urethral-insertion member 4, and on the distal side of the distal-most end of the urethral-insertion member 4.

Also, the puncture apparatus 1' includes a male screw 61. At the positional region of the supporting member 2 corresponding to that of the tubular body 35, there is formed a female screw portion 21 having a female screw to threadably engage the male screw 61.

When rotating the male screw 61 in a predetermined direction, the distal end of that male screw 61 pressure-contacts the tubular body 35, and the movement of the tubular body 35 with respect to the supporting member 2 is blocked. Also, when rotating the male screw 61 in the reverse direction with respect to the abovementioned direction, the distal end of that male screw 61 is separated from the tubular body 35 and the movement of the tubular body 35 with respect to the supporting member 2 becomes possible.

The male screw 61 and the female screw portion 21 constitute a lock unit for changing-over between a state in which the tubular body 35 is movable with respect to the supporting member 2 and a state in which the movement of the tubular body 35 is blocked.

Also, on the outer circumferential surface of the tubular body 35, there is provided a scale which indicates a distance from a reference position of the center 311 of the puncture needle 31 in the axial direction of the axial portion 33 (regarding the center 311, see FIG. 2).

Also, the urethral-insertion member 4 is a solid bar-shaped member. The distal portion of the urethral-insertion member 4 is rounded. Thus, it is possible to insert the urethral-insertion member 4 smoothly into the inside of the urethra. Needless to say, it is possible for the urethral-insertion member 4 to be formed similarly as that of the first embodiment.

This second embodiment of the puncture apparatus 1' is able to obtain similar effects as those of the aforementioned first embodiment.

Figure 13:
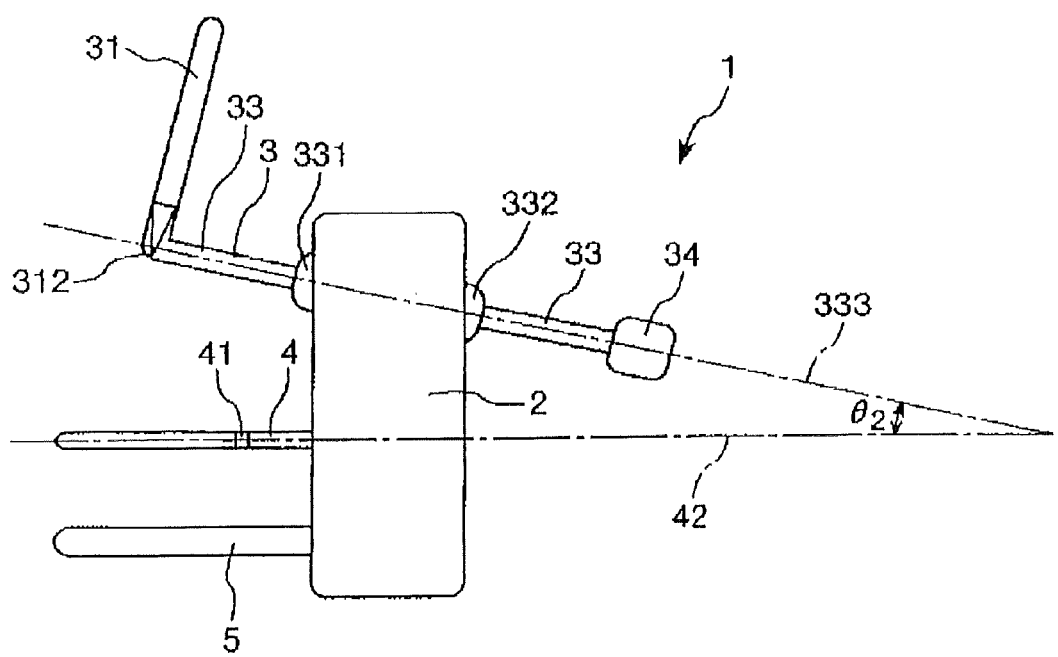
FIG. 13 is a side view of a third embodiment, disclosed by way of example, of a puncture apparatus disclosed here.

FIG. 13 illustrates a third embodiment representing another example of the puncture apparatus disclosed here. The following description of this embodiment will be set forth assuming that the left side in FIG. 13 is the "distal end" and the right side in FIG. 13 is the "proximal end".

The following description of the third embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 13, in the puncture apparatus 1" of the third embodiment, the axis 333 of the axial portion 33 of the puncture member 3 is inclined with respect to the axis 42 such that the distance of separation between the axis 333 and the axis 42 of the urethral-insertion member 4 increases toward the distal side. Thus, it is possible to bury the implant 8 by being inclined.

The axis 42 of the urethral-insertion member 4 and the axis of the vaginal-insertion member 5 are parallel, and the axis 333 of the axial portion 33 of the puncture member 3 is inclined with respect to the axis of the vaginal-insertion member 5 such that the distance of separation between the axis 333 and the axis of the vaginal-insertion member 5 increases toward the distal side.

It is preferable for the inclination-angle θ2 of the axis 333 with respect to the axis 42 to be around 20° to 60°, more preferably around 30° to 45°, and still more preferably around 35° to 40°. Thus, it is possible to carry out the puncture of the puncture needle 31 relatively easily, and concurrently it is possible to realize a shorter puncture-distance.

To explain in more detail, by setting the inclination angle θ2 to be within the aforesaid range, it is possible for the puncture needle 31 to widely capture the right-left obturator foramens 400a, 400b of the pelvis planarly and it is possible to widely secure the puncture space of the puncture needle 31. More specifically, in a state of setting the patient to be at a predetermined body position (dorsosacral position), it is possible to puncture the puncture needle 31 comparatively toward the perpendicular direction with respect to the right-left obturator foramens 400a, 400b of the pelvis. Therefore, it is possible to carry out the puncture of the puncture needle 31 rather easily. In addition, by puncturing the puncture needle 31 comparatively toward perpendicular direction with respect to the obturator foramens 400a, 400b, the puncture needle passes a shallow portion of the tissue, so that it is possible for the needle tip of the puncture needle 31 to pass between the right-left obturator foramens 400a, 400b by a shorter distance. It is possible for the puncture needle 31 to pass comparatively near the pubic-bone connection of the obturator foramens 400a, 400b and preferably through a safety zone, so that it is possible to puncture the region safely in which there are fewer nerves or blood vessels for avoiding injuries. Therefore, there can be obtained a state of lower invasion and it is possible to burden the patient to a lesser degree. In this manner, by setting the inclination angle θ2 in the aforesaid range, it is possible to carry out the puncture of the puncture needle 31 to the patient more properly. On the other hand, in a case in which the inclination angle θ2 is less than the aforesaid lower limit or exceeds the aforesaid upper limit, depending on the individual differences of the patients, the postures during the procedures and the like, there can occur a situation in which it is not possible for the puncture needle 31 to widely capture the obturator foramens 400a, 400b planarly, a situation in which it is not possible to shorten the puncture path adequately and so on. Therefore, it is preferable for the puncture needle 31 to be punctured toward the perpendicular direction with respect to the right-left obturator foramens 400a, 400b of the pelvis.

Also, by carrying out the puncture in the abovementioned angle, it becomes easier to aim the tissue between the mid-urethra indicating the middle positional portion in the length direction of the urethra and the vagina. The position between the mid-urethra and the vagina is a position suitable as the region at which the implant 8 is to be buried and the treatment of the urinary incontinence is to be carried out. More preferably, if the puncture is carried out in a state of manipulating the position so as to arrange a position of the urethra or the vagina, or both, it is rather easy to puncture a position between the mid-urethra and the vagina. It is preferable to move the urethra or the vagina, or both to the predetermined position before passing the puncture member at the position between the mid-urethra and vagina. Moving the urethra or the vagina, or both may be for example pressing/pulling toward the inside/outside of the body. The means for pushing-in either one of the urethra and the vagina toward the inside of the body moves, for example, the urethral-insertion member 4 and/or the vaginal insertion member 5 toward the inside of the body before the puncture member as far as a predetermined position along each of the axes after setting a state in which the insertion member is inserted to a proper position. The urethral-insertion member 4 and/or the vaginal insertion member 5 may have a suction mechanism for sucking the inner wall of the urethra or the vagina. The suction mechanism may hold the position of the urethral-insertion member 4 and/or the vaginal insertion member 5. When the urethral-insertion member 4 and/or the vaginal insertion member 5 may be moved toward the inside or the outside of the body, the urethra and/or the vagina may be moved along the member 4 and/or the member 5. At that time, by attaching a visible marker or such a marker which can be imaged under a noninvasive monitoring of the inside of the body depending on such as X-ray, ultrasound or the like onto the urethral-insertion member 4 and/or onto the vaginal insertion member 5, it is possible to recognize the movement distance of the member.

By puncturing the puncture needle 31 perpendicularly with respect to the right-left obturator foramens 400a, 400b of the pelvis in a state in which the position is prolapsed so as to press at least one of the urethra and the vagina toward the inside of the body, it is possible to form the path at a position suitable for the indwelling of the implant 8.

It is preferable that the orbit of the puncture needle 31 is set so as to pass the safety zone of the right-left obturator foramens 400a, 400b of the pelvis, that at least one of the urethra and the vagina is prolapsed toward the inside of the body such that the orbit is positioned between the mid-urethra and the vagina, and that the path will be formed by executing the puncture along the orbit of the puncture needle 31.

The urethral-insertion member 4 is a solid bar-shaped member. Also, the distal portion of the urethral-insertion member 4 is rounded. Thus, it is possible to insert the urethral-insertion member 4 smoothly into the inside of the urethra. It is possible for the urethral-insertion member 4 to be formed similarly as that of the first embodiment.

The puncture apparatus 1″ according to this third embodiment is able to obtain similar effects as those of the first embodiment described above.

It is possible for the axis 42 of the urethral-insertion member 4 and the axis of the vaginal-insertion member 5 not to be parallel to each other.

Figure 20:
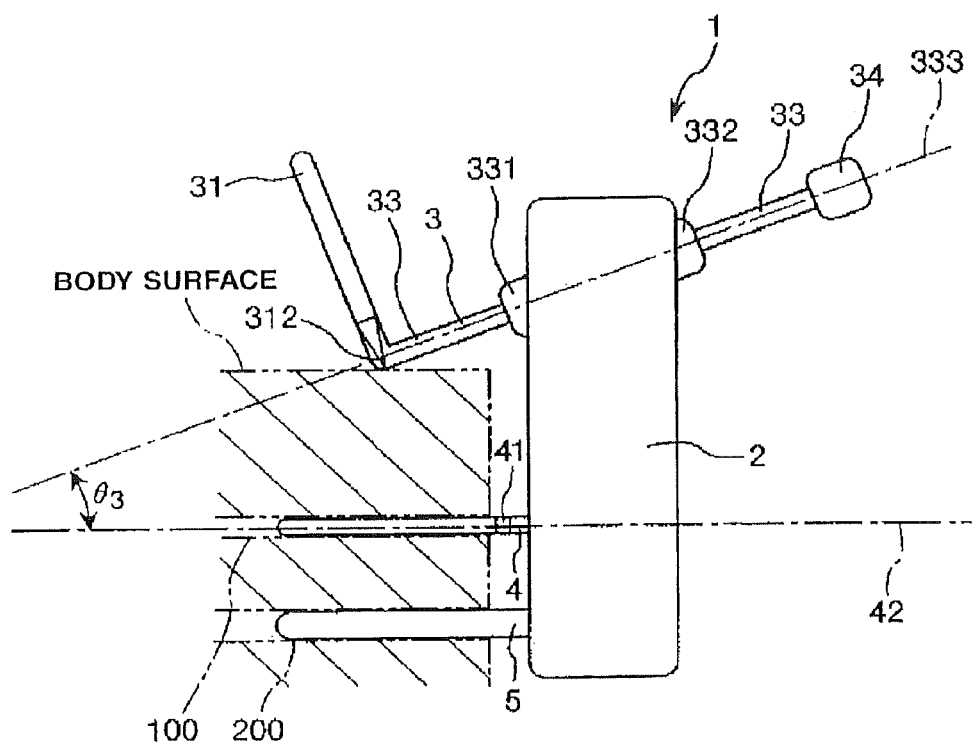
FIG. 20 is a side view of a fourth embodiment, disclosed by way of example, of a puncture apparatus disclosed here.

FIG. 20 illustrates a fourth embodiment representing another example of the puncture apparatus disclosed here. The following description of this embodiment will be set forth assuming that the left side in FIG. 20 is the "distal end" and the right side in FIG. 20 is the "proximal end".

The following description of the fourth embodiment will focus primarily on aspects or features of the puncture apparatus different from those of the third embodiment described above. Features and aspects of this fourth embodiment of the puncture apparatus that are similar to those described above are identified by common reference numerals, and a detailed description of such aspects and features is not repeated.

As shown in FIG. 20, in the puncture apparatus 1′ of the fourth embodiment, the axis 333 of the axial portion 33 of the puncture member 3 is inclined with respect to the axis 42 such that the distance of separation between the axis 333 and the axis 42 of the urethral-insertion member 4 decreases toward the distal side. Thus, it is possible to bury the implant 8 by being inclined.

The axis 42 of the urethral-insertion member 4 and the axis of the vaginal-insertion member 5 are in parallel and the axis 333 of the axial portion 33 of the puncture member 3 is inclined with respect to the axis of the vaginal-insertion member 5 such that the separated distance between the axis 333 and the axis of the vaginal-insertion member 5 decreases toward the distal side.

The preferable range of the inclination-angle θ3 of the axis 333 with respect to the axis 42 is similar to the preferable range of the inclination-angle θ2 of the third exemplified embodiment.

This puncture apparatus 1′ is able to obtain similar effects as those described above regarding the third embodiment.

Note that the axis 42 of the urethral-insertion member 4 and the axis the vaginal-insertion member 5 are allowed to be not in parallel.

Figure 21:
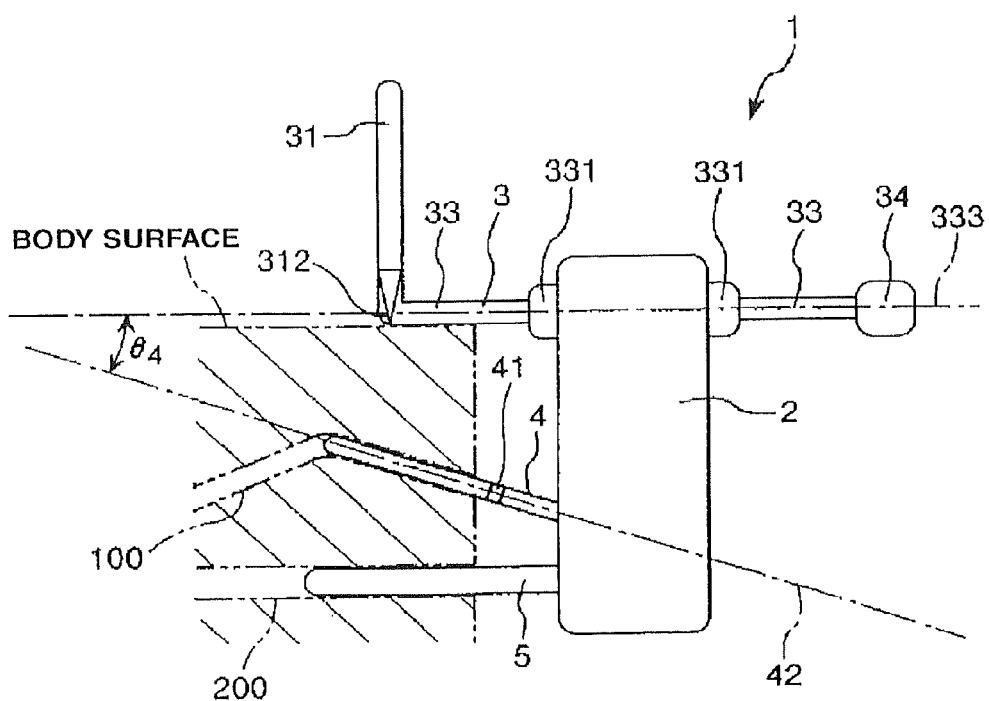
FIG. 21 is a side view of a fifth embodiment, disclosed by way of example, of a puncture apparatus disclosed here

FIG. 21 illustrates a fifth embodiment representing another example of the puncture apparatus disclosed here. The following description of this embodiment will be set forth assuming that the left side in FIG. 21 is the "distal end" and the right side in FIG. 21 is the "proximal end".

The following description of the fifth embodiment will focus primarily on aspects or features of the puncture apparatus different from those of the third embodiment described above. Features and aspects of this embodiment that are similar to those described above in the third embodiment are identified by common reference numerals, and a detailed description of such aspects and features is not repeated.

As shown in FIG. 21, in the puncture apparatus 10 of the fifth embodiment, the axis 42 of the urethral-insertion member 4 is inclined with respect to the axis 333 such that the distance of separation between the axis 42 and the axis 333 of the axial portion 33 of the puncture member 3 decreases toward the distal side. In other words, the axis 333 of the axial portion 33 of the puncture member 3 is inclined with respect to the axis 42 such that the distance of separation between the axis 333 and the axis 42 of the urethral-insertion member 4 decreases toward the distal side. Thus, it is possible to bury the implant 8 by being inclined.

The axis 333 of the axial portion 33 of the puncture member 3 and the axis of the vaginal-insertion member 5 are parallel, and the axis 42 of the urethral-insertion member 4 is inclined with respect to the axis of the vaginal-insertion member 5 such that the distance of separation between the axis line 333 and the axis line of the vaginal-insertion member 5 increases toward the distal side.

The preferable range of the inclination-angle θ4 of the axis line 42 with respect to the axis 333 (inclination-angle of the axis 333 with respect to the axis 42) is similar to the preferable range of the inclination-angle θ2 discussed above regarding the third embodiment.

This puncture apparatus 10 is able to obtain similar effects as those described above regarding the third embodiment.

It is possible for the axis 42 of the urethral-insertion member 4 to be inclined with respect to the axis 333 such that the distance of separation between the axis 42 and the axis 333 of the axial portion 33 of the puncture member 3 increases toward the distal side. In other words, it is possible for the axis 333 of the axial portion 33 of the puncture member 3 to be inclined with respect to the axis 42 such that the distance of separation of the axis 333 and the axis 42 of the urethral-insertion member 4 increases toward the distal side.

Figure 14:
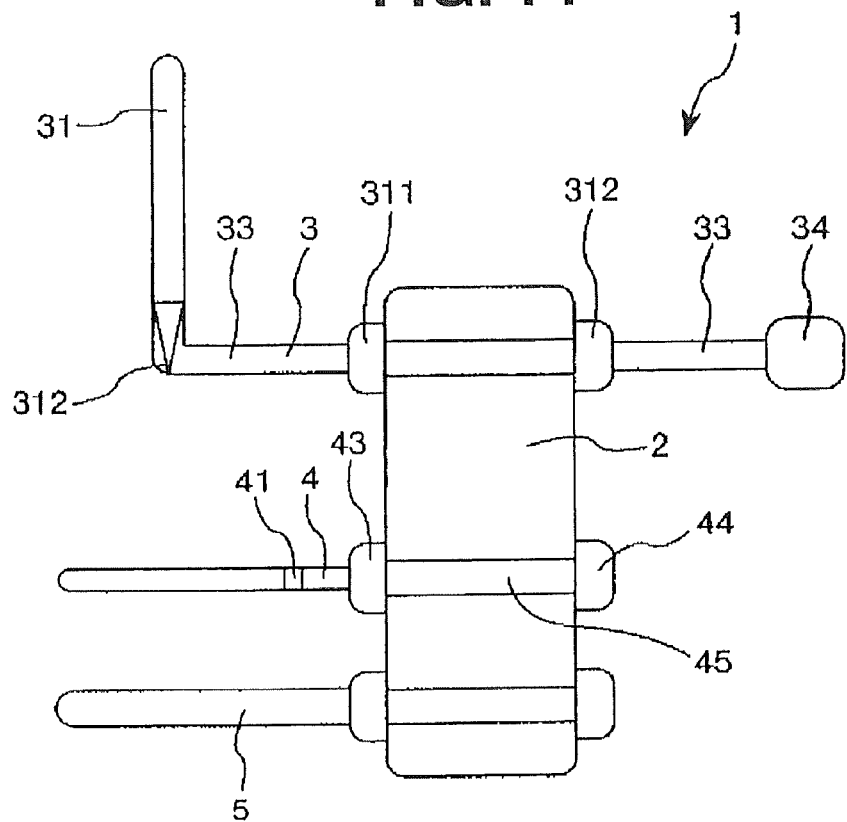
FIG. 14 is a side view of a sixth embodiment, disclosed by way of example, of a puncture apparatus disclosed here.
Figure 15:
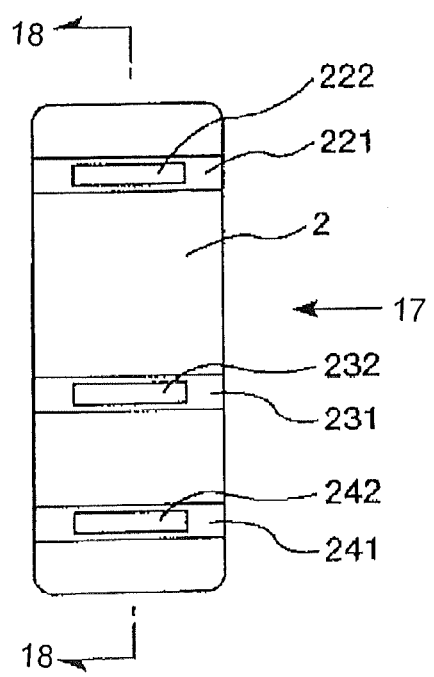
FIG. 15 is a side view showing a supporting member of the puncture apparatus shown in FIG. 14.

FIGS. 14-18 illustrate a sixth embodiment representing another example of the puncture apparatus disclosed here. FIG. 16A is a front elevational view, that is, a view seen from the upside in FIG. 14. Also, either one of FIG. 16B and FIG. 16C is a view seen from a direction of an arrow 16B, 16C in the urethral-insertion member shown in FIG. 16A, in which for the attachment piece of the urethral-insertion member shown in FIG. 16C, there is shown a state thereof in which the attachment piece is rotated by 90° with respect to the attachment piece of the urethral-insertion member shown in FIG. 16B. The following explanation is set forth assuming that the left side in FIG. 14, FIG. 15, FIG. 16A is the "distal end" and the right side is the "proximal end".

The following description of the sixth embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

In the puncture apparatus 10′ of the sixth embodiment shown in FIG. 14, the puncture member 3, the urethral-insertion member 4 and the vaginal-insertion member 5 are freely detachable with respect to supporting member 2 respectively. More specifically, the axial portion 33 of the puncture member 3, the urethral-insertion member and the vaginal-insertion member 5 are supported by the supporting member 2 in a freely detachable manner respectively.

Also, the urethral-insertion member 4 is a solid bar-shaped member, and the distal portion of the urethral-insertion member 4 is rounded. Thus, it is possible to insert the urethral-insertion member 4 smoothly into the inside of the urethra. Needless to say, it is possible for the urethral-insertion member 4 to be formed similar to that of the first embodiment described above.

As shown in FIG. 14, FIG. 15, FIG. 17 and FIG. 18, the supporting member 2 includes a groove 221 to which the puncture member 3 is attached or in which the puncture member 3 is positioned; a through-hole 222 provided in the inside of the groove 221; a groove 231 to which the urethral-insertion member 4 is attached or in which the urethral-insertion member 4 is positioned; a through-hole 232 provided in the inside of the groove 231; a groove 241 to which the vaginal-insertion member 5 is attached or in which the vaginal-insertion member 5 is positioned; and a through-hole 242 provided in the inside of the groove 241. The grooves 221, 231, 241 are formed respectively on the front side of the supporting member 2 in the FIG. 15 illustration and extend from the distal end to the proximal end of the supporting member 2.

The construction or configuration of the detachable mechanisms of the puncture member 3, the urethral-insertion member 4 and the vaginal-insertion member 5 with respect to the supporting member 2 is similar to one another, so that hereinafter, with regard to each detachable arrangement, the detachable mechanism of the urethral-insertion member 4 will be explained representatively.

As shown in FIG. 14 and FIG. 16, in a state of being attached to the supporting member 2 (hereinafter, also referred to as "attachment state"), the urethral-insertion member 4 is formed with a flange 43 and a flange 44 on the distal side and on the proximal side respectively through that supporting member 2, and the axial movement of the urethral-insertion member 4 with respect to the supporting member 2 is blocked by these flanges 43, 44. The flange 44 is arranged at the proximal portion of the urethral-insertion member 4.

Also, a region 45 between the flange 43 and the flange 44 of the urethral-insertion member 4 is thicker than the region on the distal side from the flange 43 of the urethral-insertion member 4. Also, the cross-sectional shape of the region 45 between the flange 43 and the flange 44 of the urethral-insertion member 4 is square shape according to the constitution shown in the drawing.

Figure 16A:
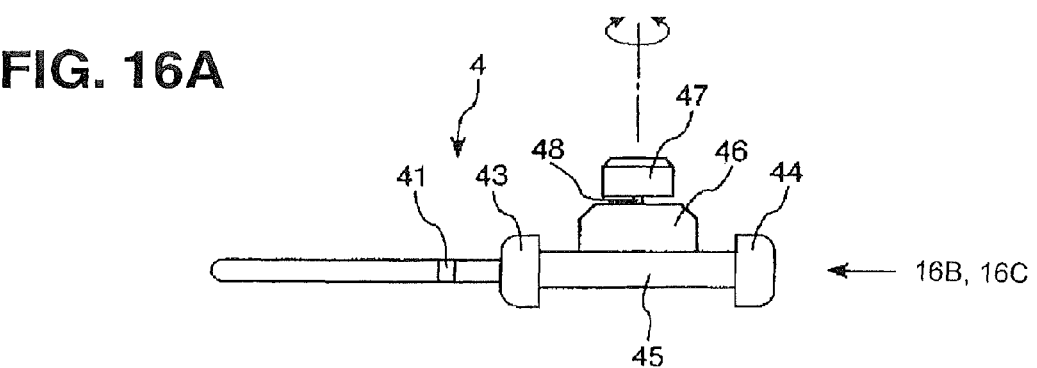
FIGS. 16A to 16C are views showing a urethral-insertion member of the puncture apparatus shown in FIG. 14.

At the region 45 between the flange 43 and the flange 44 of the urethral-insertion member 4, there is formed a protruding portion 46, in the attachment state, which protrudes toward the rear side from the front side of the drawing of FIG. 14, that is, which protrudes toward the upper side in FIG. 16A. At the protruding portion 46, there is located an attachment piece 48 through a freely rotatable axis member 47. This attachment piece 48 has a flattened shape. The attachment piece 48 protrudes toward the upper side in FIG. 16A.

Figure 16B:
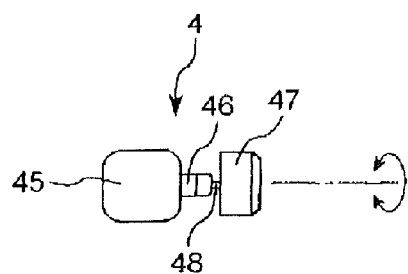
Figure 16C:
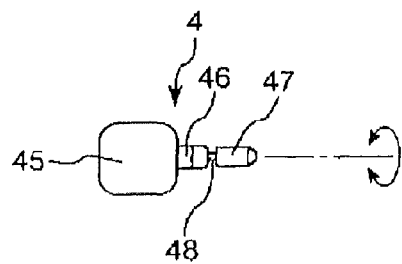
Figure 17:
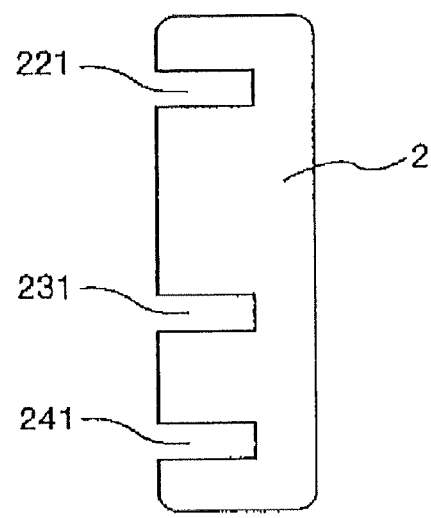
FIG. 17 is a view seeing the puncture apparatus from a direction of an arrow 17 shown in FIG. 15.

When attaching the urethral-insertion member 4 to the supporting member 2, the attachment piece 48 of the urethral-insertion member 4 is set in a state shown in FIG. 16C and the attachment piece 48 is inserted from the groove 231 of the supporting member 2 and is passed through the through-hole 232. Then, at that time, the region 45 between the flange 43 and the flange 44 of the urethral-insertion member 4 is inserted into the groove 231 of the supporting member 2 and concurrently, the protruding portion 46 is inserted into the through-hole 232.

Figure 18:
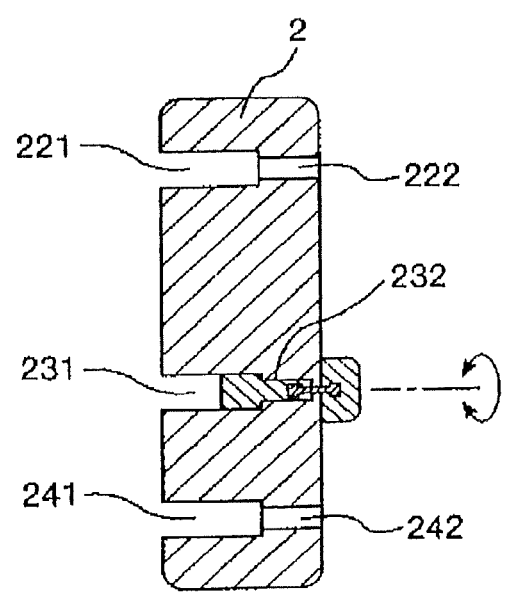
FIG. 18 is a cross-sectional view along the section line 18-18 in FIG. 15.

Next, as shown in FIG. 18, the attachment piece 48 of the urethral-insertion member 4 is set in a state shown in FIG. 16B by being rotated by 90°. Thus, while the region 45 between the flange 43 and the flange 44 of the urethral-insertion member 4 is attached onto or set into the bottom surface of the groove 231, the attachment piece 48 is attached or set onto the surface on the right side of the urethral-insertion member 4 in FIG. 18 and so the attachment and detachment of the urethral-insertion member 4 with respect to the supporting member 2 is blocked.

Also, when removing the urethral-insertion member 4 from the supporting member, the attachment piece 48 of the urethral-insertion member 4 is set in a state shown in FIG. 16C and the urethral-insertion member 4 is made to move toward the left side in FIG. 18. Thus, it is possible to remove the urethral-insertion member 4 from the supporting member 2.

This puncture apparatus 10' is able to obtain similar effects as those of the first embodiment described above. It is possible to apply this sixth embodiment to the second to fifth embodiments described above to provide the freely detachable arrangement of the puncture member 3, the urethral-insertion member 4 and/or the vaginal-insertion member 5 with respect to the supporting member 2.

In this embodiment, the puncture member 3, the urethral-insertion member 4 and the vaginal-insertion member 5 are freely detachable with respect to the supporting member 2. But the apparatus is not limited to this configuration and it is possible, for example, for only one or only two of the puncture member 3, urethral-insertion member 4 and the vaginal-insertion member 5 to be freely detachable with respect to the supporting member 2. In this case, it is preferable for at least the puncture member 3 to be freely detachable with respect to the supporting member 2.

Figure 22A:
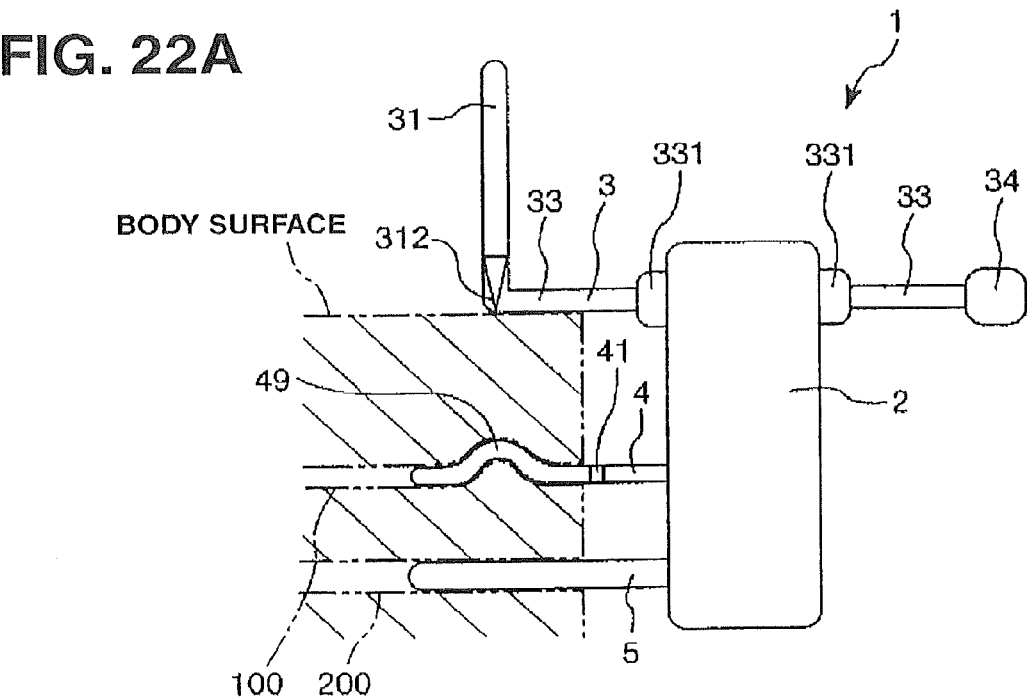
FIGS. 22A to 22C are side views of a seventh embodiment, disclosed by way of example, of a puncture apparatus disclosed here
Figure 22B:
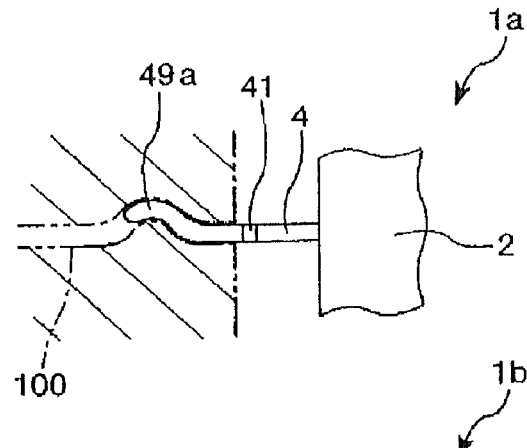
Figure 22C:
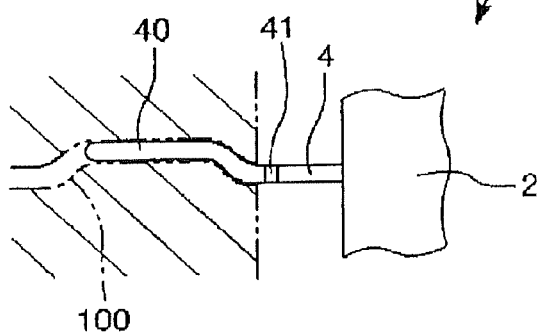

FIGS. 22A-22C illustrates a seventh embodiment representing another example of the puncture apparatus disclosed here. The following description of this embodiment will be set forth assuming that the left side in FIGS. 22A-22C is the "distal end" and the right side in FIGS. 22A-22C is the "proximal end".

The following description of the seventh embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 22A, in the puncture apparatus 10' of the seventh embodiment, the urethral-insertion member 4 is configured so that a midway portion of the urethral-insertion member 4 is bent and includes a protruding portion 49 which protrudes toward the direction away from the vaginal-insertion member 5.

It is possible by this protruding portion 49 to widen the distance between the urethra 100 and the vagina 200 and thus, it is possible to reliably prevent a phenomenon in which the puncture needle 31 will puncture the urethra 100 or the vaginal wall of the vagina 200. Similar effects are obtained by the puncture apparatuses 10'a, 10'b described below.

In the puncture apparatus 10'a shown in FIG. 22B, the length of the urethral-insertion member 4 becomes short with respect to that of the puncture apparatus 10' shown in FIG. 22A and there is included a protruding portion 49a at the distal portion of the urethral-insertion member 4. The protruding portion 49a is a portion which is formed by bending the urethral-insertion member 4 and which protrudes toward the direction apart from the vaginal-insertion member 5, in which it is constituted to be shorter than the protruding portion 49 of the puncture apparatus 1.

In this puncture apparatus 10'a, it is possible to prevent an excessive insertion of the urethral-insertion member 4 into the urethra 100.

In the puncture apparatus 10'b shown in FIG. 22C, the urethral-insertion member 4 includes a linear shaped portion 40 forming a linear shape which is positioned at the regional portion from the midway to the distal end thereof and which is on the side apart from the vaginal-insertion member 5 compared with the proximal portion. Note that there is no limitation in particular for the length of the linear shaped portion 40 and the length is set arbitrarily in response to various conditions.

These puncture apparatuses 10', 10'a, 10'b are able to obtain similar effects as those described above regarding the first embodiment. And it is possible to apply this seventh embodiment to the other respective embodiments described above.

Figure 23:
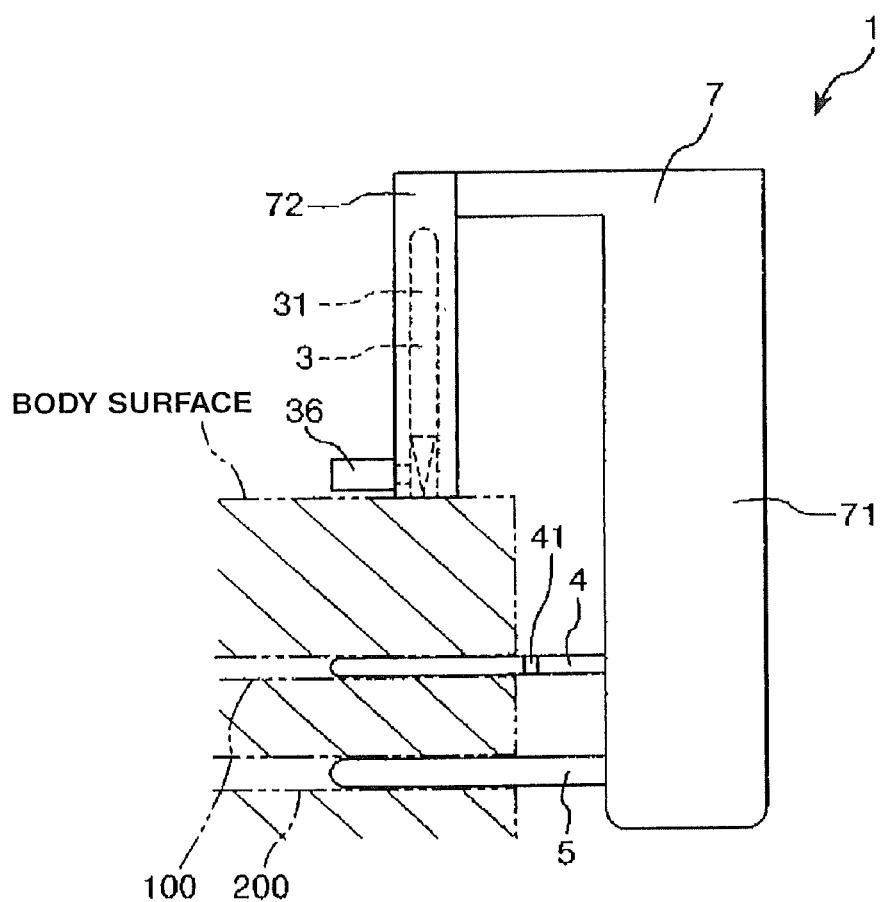
FIG. 23 is a side view of an eighth embodiment, disclosed by way of example, of a puncture apparatus disclosed here
Figure 24:
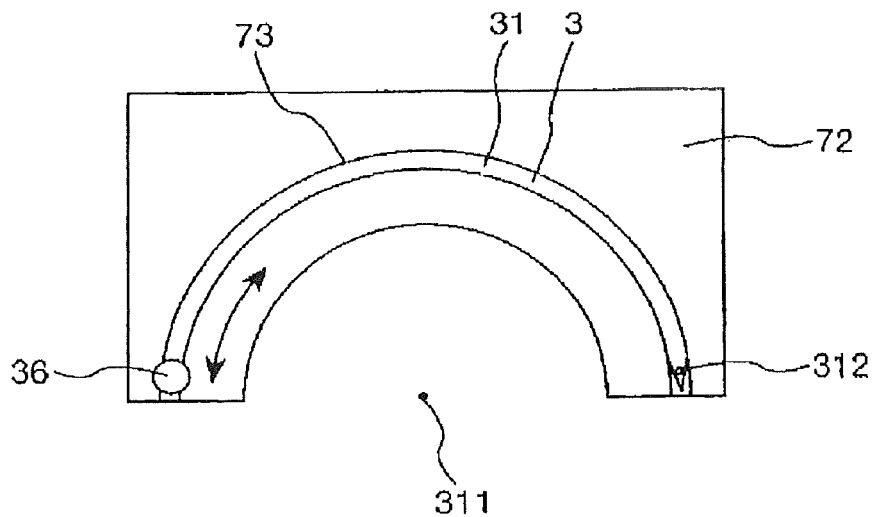
FIG. 24 is a front elevational view showing a puncture member and a second supporting portion of the puncture apparatus shown in FIG. 23.

FIGS. 23 and 24 illustrate an eighth embodiment representing another example of the puncture apparatus disclosed here, with FIG. 23 representing a side view of the apparatus and FIG. 24 showing a puncture member and a second supporting portion of the puncture apparatus shown in FIG. 23 as seen from the front. The following description of this embodiment will be set forth assuming that the left side in FIG. 23 is the "distal end" and the right side in FIG. 23 is the "proximal end".

The following description of the eighth embodiment will focus primarily on aspects or features of the puncture apparatus different from those of the first embodiment described above. Features and aspects of this embodiment that are similar to those described above in the first embodiment are identified by common reference numerals, and a detailed description of such aspects and features is not repeated.

As shown in FIG. 23 and FIG. 24, in the puncture apparatus 10" of the eighth embodiment, a supporting member (restriction means) 7 includes a first supporting portion 71 for supporting the urethral-insertion member 4 and the vaginal-insertion member 5; and a second supporting portion 72 on the distal side of the first supporting portion 71 and which freely rotatably supports the puncture member 3.

The puncture member 3 includes a puncture needle 31 and a grasping unit 36 provided at the proximal portion of the puncture needle 31. The grasping unit 36 protrudes toward the distal side from the proximal portion of the puncture needle 31, that is, toward the left side in FIG. 23.

In the second supporting portion 72, there is formed a groove (arc-shaped groove) 73 having a shape corresponding to the puncture needle 31, and the puncture needle 31 is inserted (housed) inside the groove 73 in a freely rotatable or freely movable manner. More specifically, the puncture needle 31 is configured and housed to slide along the inner surface of the groove 73, and the puncture needle 31 moves rotationally (along an arc), with the center 311 serving as the rotary center by sliding along the inner surface of the groove 73. The second supporting portion 72 thus serves as a guide member for guiding the puncture needle 31 along the groove 73. When moving the puncture needle 31, that is, the puncture member 3 rotationally, the grasping unit 36 is grasped and the rotational operation of the puncture member is carried out. Regarding the center 311, it is possible to apply the features of axial portion 33 in the other embodiments.

The inside of the groove 73 is larger than the opening of the entrance to the groove. It is thus possible to prevent the puncture needle 31 from dropping-out from the inside of the groove 73 (e.g., by configuring the portion of the needle positioned in the groove to be slightly larger than the size of the opening of the entrance of the groove).

This puncture apparatus 10" obtains similar effects as those described above regarding the first embodiment. It is possible to apply this eighth embodiment to the respective other embodiments described above.

The guide member is not limited to the specific member used in this embodiment. It is possible, for example, to employ members described below and referred to as constitution 1, constitution 2 and constitution 3.

In constitution 1, a convex portion (guide portion) is provided on the puncture needle, the puncture needle is not housed in the groove of a guide member, the convex portion is housed in the guide member, and this convex portion is guided along the groove.

In constitution 2, the guide member includes, for example, a rail (rib) forming an arc shape, and there is provided, on the puncture needle, a guide portion which is engaged with the rail and which is movable along this rail. The guide portion is guided along the rail.

In constitution 1, the guide member includes a plurality of pin-pairs constituted by pin-pairs each of which is arranged by being separated as much as a predetermined distance, for example, a distance which is a little bit longer than the outer diameter of the puncture needle and the puncture needle is configured to move between each of the pin-pairs. The respective pin pairs are arranged, for example, in an arc shape and the puncture needle is guided by these respective pin-pairs.

Figure 25:
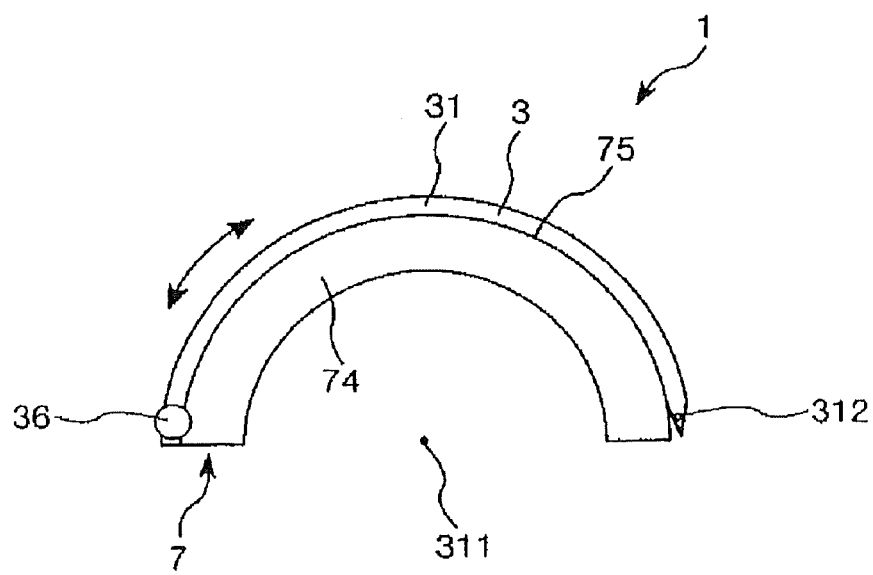
FIG. 25 is a front elevational view showing a puncture member and a second supporting portion of a supporting member in a ninth embodiment of the puncture apparatus disclosed here.

FIG. 25 illustrates a puncture member and a second supporting portion of a supporting member in a ninth embodiment of the puncture apparatus disclosed here. In the description below, the upper side in FIG. 25 is "up" and the lower side is "down".

The following description of the ninth embodiment will focus primarily on aspects or features of the puncture apparatus different from those of the eighth embodiment described above. Features and aspects of this embodiment that are similar to those described above in the eighth embodiment are identified by common reference numerals, and a detailed description of such aspects and features is not repeated.

As shown in FIG. 25, in the puncture apparatus 10''' in the ninth embodiment, a second supporting portion 74 of the supporting member 7 forms an arc shape. More specifically, an upper surface 75 of the second supporting portion 74 forms a shape corresponding to the puncture needle 31.

Also, the puncture needle 31 is placed or positioned on the upper surface 75 of the second supporting portion 74. The puncture needle 31 is slidable along the upper surface 75 of the second supporting portion 74, and the puncture needle 31 moves rotationally (along an arc) by making the center 311 thereof as the rotary center by sliding along the upper surface 75. The second supporting portion 72 thus constitutes the guide member.

This puncture apparatus 10''' is able to obtain similar effects as those described above regarding the eighth embodiment. And it is possible to apply this ninth embodiment to the respective other embodiments described above.

As described above, the puncture apparatus disclosed here is explained based on the embodiments shown in the drawings, but the present invention is not limited by these embodiments, and it is possible to replace the constitution of each portion by a different or arbitrary constitution having a similar function. It is also possible to add other arbitrary constituent elements.

Figure 26:
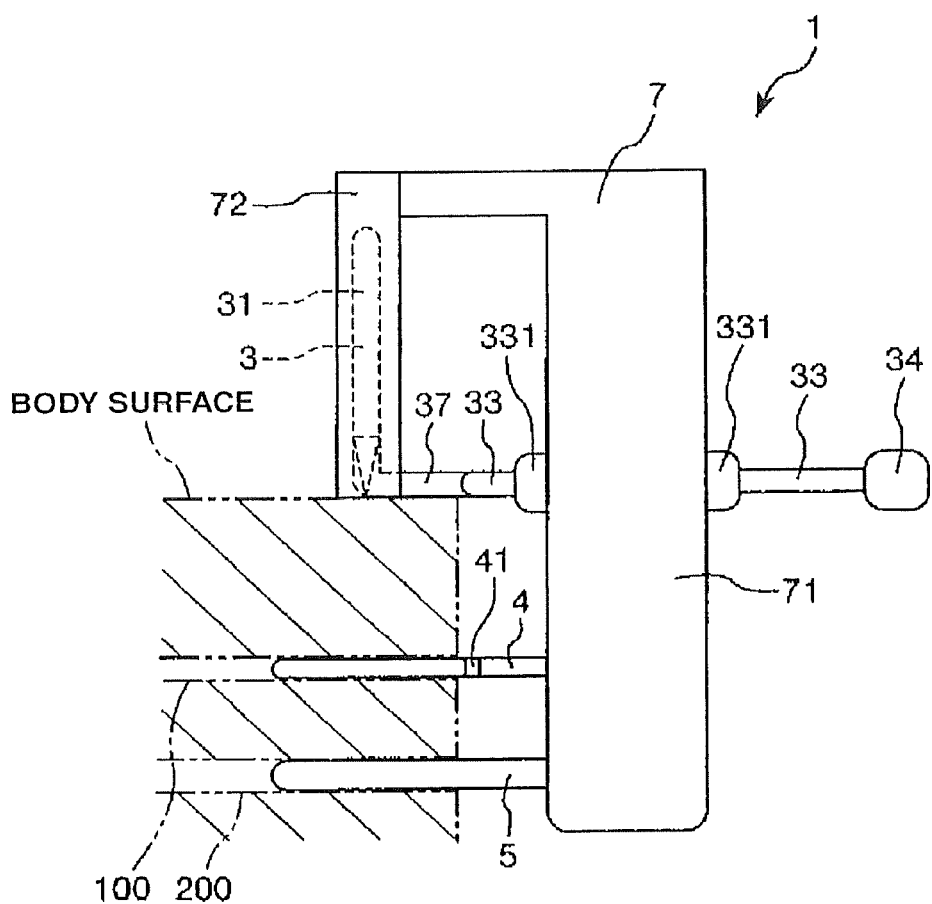
FIG. 26 is a side view showing another example of the puncture apparatus of the present invention.
Figure 27:
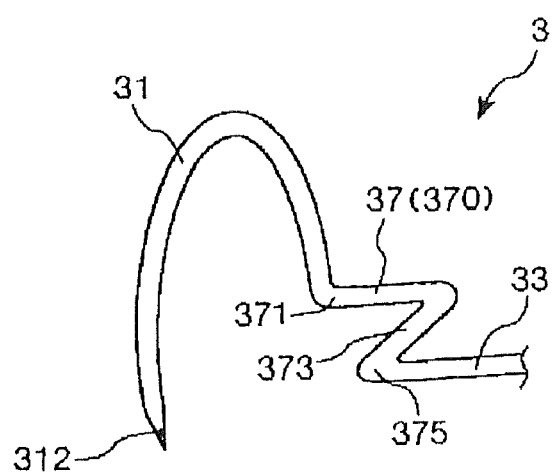
FIG. 27 is a perspective view showing a puncture member of the puncture apparatus shown in FIG. 26.

Also, it is possible to employ an arrangement in which two or more constructions or constitutions within the respective embodiments are combined. In particular, as shown in FIG. 26, by combining the first embodiment (see FIG. 1 and FIG. 2) and the eighth embodiment (see FIG. 23 and FIG. 24) and by providing the second supporting portion 72 of the eighth embodiment, which supports the puncture member 3 in a freely rotatable manner, in the puncture apparatus 1 of the first embodiment, it is possible to restrict the orbit exactly when puncturing the living body tissue by the puncture member 3 and thus, a more accurate puncture becomes possible. The interlock portion 37 of the puncture member 3 of the puncture apparatus 1, which is shown in this FIG. 26, forms an L-shape as shown in FIG. 27. The axial portion 33 of the puncture member 3 is located or mounted on the first supporting portion 71 in a freely rotatable manner.

Here, depending on the patient, the region, between the position at which the puncture needle 31 is inserted into (enters) the body from the body surface and the position at which the needle protrudes back outside the body from the body surface, rises and the center of the arc of the puncture needle 31 is positioned at the patient side compared with the body surface of the patient, so that there may be a situation in which the puncture apparatus 1 cannot be correctly placed at a predetermined position. Such a rising can be seen many times for heavy patients. On the other hand, for a skinny patient or the like, caused by the fact that the interlocking region or the vicinity of such region is depressed, it becomes a state in which there occurs a phenomenon of rising relatively and there occurs a situation in which the center portion of the patient interferes with the puncture needle 31, so that a situation arises in which that state prevents the puncture operation. Even in such a case, by setting the interlock portion 37 to be in an L-shape, it is possible to help prevent the interlock portion 37 and the axis portion 33 from interfering with the rising region of the patient and it is possible to carry out the puncture operation by the puncture needle 31 rather easily and also reliably. The interlock portion 37 is composed of a distal portion 371 and a proximal portion 373.

The distal portion 371 extends from the end portion at the opposite side of the needle tip of the puncture needle 31 toward the perpendicular direction with respect to the plane including the arc of the puncture member 3 (with respect to the plane on which the puncture member 3 moves rotationally) (with respect to the orbital plane of the arc). The proximal portion 373 extends from the proximal portion of the distal portion 371 in the perpendicular direction toward the axial portion 33. More specifically, the proximal portion 373 extends from the proximal portion of the distal portion 371 in a direction perpendicular to the axial portion 33. The axial portion 33 extends perpendicularly from the center of the arc of the puncture needle 31 with respect to the plane including the arc of the puncture member 3.

It is also possible for the puncture apparatus 10''' shown in FIG. 26 to use one of the urethral-insertion member and the vaginal insertion member if it is possible to carry out the puncture by avoiding the urethra 100 and the vagina 200 carefully by specifying the positions of the urethra 100 and the vagina 200, for example, by monitoring with X-ray, ultrasound or the like. In this case, it is possible for the puncture apparatus 10''' shown in FIG. 26 to be formed to have constituent elements of a puncture needle 31 which is placed freely rotatably, which includes a bent region and which punctures living body tissue; an axial portion 33 which extends from the end portion at the opposite side of the needle tip of the puncture needle 31 through the L-shaped interlock portion 37; and a supporting portion 71 by which the axial portion 33 is placed freely rotatably.

In the configuration shown in FIG. 27, the interlock portion 37 forms an L-shape, but the shape of the interlock portion 37 is not so limited, and it is possible to employ a configuration which is formed, for example, by a linear shape, a curved shape, a shape made by combining a linear shape and a curved shape, or the like in which the portion is connected to the axial portion 33 so as not to interfere with the region of the rising portion of the aforesaid patient.

Also, in the present invention, it is possible, for example, to employ a configuration in which the vaginal-insertion member is omitted and the restriction means is provided so as to restrict only the positional relation between the puncture needle (puncture member) and the urethral-insertion member.

In the embodiments of the puncture apparatus described above, the orbit or path of movement of the puncture member is specified according to the positional relation with respect to the urethral-insertion member. But it is also possible to specify the orbit or path of movement according to the positional relation with respect to the vaginal insertion member. For example, it is possible to employ a configuration in which the orbit or path of movement of the puncture member passes a position which is on the position side near from the center point of the orbit and which is spaced from the vaginal insertion member by a predetermined distance. Thus, for example, with respect to a patient whose distance between the mid-urethra and the vagina was measured beforehand, it is possible for the orbit or movement path of the puncture member to pass a position which is on the position side near from the center point of the orbit and which is spaced from the vaginal insertion member by a distance shorter than the distance between the mid-urethra and the vagina.

The description above describes various embodiments in which the puncture apparatus is used in an apparatus that buries or positions a buriable implant for treatment of the woman's urinary incontinence into the inside of the living body. But the use of the puncture apparatus is not limited in this regard.

For example, the target to be applied with the puncture apparatus discloses here includes an excretory disorder along with the weakening of the pelvic floor muscle group (urinary urgency, frequent urination, urinary incontinence, fecal incontinence, urinary retention, dysuria or the like), and a pelvic floor disorder including pelvic organ prolapse, vesicovaginal fistula, urethrovaginal fistula, pelvic pain or the like. In the pelvic organ prolapse, there are include disorders of cystocele, enterocele, rectocele, hysterocele and the like. Alternatively, there are included disorders of anterior vaginal prolapse, posterior vaginal prolapse, vaginal vault prolapse, vaginal apical prolapse and the like in which the naming method thereof is based on the manipulating vaginal-wall regions.

Also, in the overactive tissues, there are included bladder, vagina, uterus, bowel and the like. In the lessactive tissues, there are included bones, muscles, fascias, ligaments and the like. In particularly, in the pelvic floor disorders, there are included an obturator fascia, a coccygeus fascia, a cardinal ligament, a uterosacral ligament, a sacrotuberous ligament and the like.

For the procedure for interlocking an overactive tissue in the pelvic floor disorder with the lessactive tissue, there are included a retropubic sling surgery, a transobturator sling surgery (Transobturator Sling surgery, Transobturator Tape: TOT), a tension-free vaginal mesh (Tension-free Vaginal Mesh: TVM) surgery, a uterosacral ligament suspension (Uterosacral Ligament Suspension: USLS) surgery, a sacrospinous ligament fixation (Sacrospinous Ligament Fixation: SSLF) surgery, an iliococcygeus fascia fixation surgery, a coccygeus fascia fixation surgery, and the like.

It is possible for the puncture apparatus disclosed here to be applied to the pelvic floor disorder as follows. It is possible for the puncture apparatus used for the pelvic floor disorder to be applied with the respective constructions of the puncture apparatuses of the above-described embodiments for treating urinary incontinence. As one embodiment, there are provided with a puncture member which is freely rotatably mounted, which includes a bent region and which includes a puncture needle for puncturing living body tissue; an insertion member having a longitudinal shape, which is to be inserted into the inside of the body; and a restriction structure for restricting the positional relation between the puncture member and the insertion member such that the needle tip of the puncture needle will pass at a far-position side from the rotation center of the puncture needle compared with the insertion member when the puncture member rotates and punctures the living body tissue.

For example, in the case of a rectocele, within the pelvic organ prolapses included in the pelvic floor disorders, in which the deviation occurs by the fact that the rectum pushes the vaginal wall, the overactive tissues are the rectum and the vagina and the lessactive tissue becomes the interlock region, or a muscle, a tendon or a ligament in the vicinity thereof.

As an example, one embodiment of a procedure for forming a path for burying an implant for treating the rectocele is as follows. First, a puncture apparatus is prepared and provided with a puncture member which is freely rotatably positioned, and which includes a bent region and which includes a puncture needle for puncturing living body tissue; an insertion member having a longitudinal (elongated) shape, which is to be inserted into the inside of the living body; and a restriction structure for restricting the positional relation between the puncture member and the insertion member such that the needle tip of the puncture needle will pass a far-position side (be spaced from) from the rotation center of the puncture needle compared with the insertion member when the puncture member rotates and punctures the living body tissue. Next, the insertion member is inserted into a rectum of a patient. Further, the puncture needle of the puncture member is operated to puncture a body surface at one buttock region of the patient or at the region in the vicinity thereof, made to enter into the body, made to pass a far-position side of the rectum, made to protrude to the outside of the body from the body surface of another buttock region or from the region in the vicinity of such region, whereby there is formed a through-hole reaching the far-position side of the rectum and the another buttock region or the region in the vicinity of such region from the other buttock region or the region in the vicinity of such region. After forming the through-hole, a mesh-shaped implant is indwelled by an identical or similar method as that of the urinary incontinence described above.

For another embodiment of the procedure disclosed by way of example, there is a method in which there is prepared a puncture member which is freely rotatable, which includes a bent region and which includes a puncture needle for puncturing living body tissue; and when the puncture member is moved rotationally and the puncture needle of the puncture member punctures the living body tissue, the puncture needle is made to puncture a body surface at a buttock region of the patient or at the region in the vicinity thereof and is made to enter into the body; and the puncture member is made to pass a far-position side from the rotation center of the puncture needle compared with a rectum which is the target region, whereby the path is formed.

An another embodiment of the procedure, there is prepared a puncture tool provided with an insertion member having a longitudinal (elongated) shape, which is to be inserted into the inside of a rectum, and a puncture member which can puncture the living body tissue and which has such an orbit or movement path passing a far-position side compared with the insertion member; the insertion member is inserted into the rectum of a patient; the puncture member is made to puncture into the body surface at a buttock region of the patient or at the region in the vicinity of such region; and the puncture member is made to pass a far-position side compared with the insertion member, whereby the path is formed. The insertion member is not limited to a member which is inserted into a tubular lumen having an opening on the surface of the living body, such as a vagina, a urethra, a rectum and the like, and there can be included also a configuration in which the insertion member punctures the tissue from the surface of the living body. In case of puncturing the tissue from the surface of the living body, it is preferable for a tissue insertion member to be provided with a marker by which the position of the tissue insertion member can be confirmed or identified. By providing a marker, there can be confirmed the position at which the insertion member punctures the tissue. For the marker, it is possible to attach a visually-recognizable marker by which the insertion depth is visually recognizable. Also, for the marker, it is preferable to use a marker which is visually recognizable under a noninvasive monitoring inside the body.

The target to be applied is not limited by the pelvic floor disorder. For example, the apparatus and method are also applicable to a disorder in which position deviation of an organ occurs in the inside of the living body such as a case of an interlock hernia, an abdominal wall hernia or the like.

A puncture apparatus disclosed here generally includes a freely rotatable puncture member which includes a bent region and which includes a puncture needle for puncturing living body tissue, a urethral-insertion member having an elongated shape which is to insertable into the inside of a urethra, and restriction means for restricting the positional relation between the puncture member and the urethral-insertion member such that the needle tip of the puncture needle will pass a far-position side from the rotation center of the puncture needle compared with the urethral-insertion member when the puncture member rotates and punctures the living body tissue.

When burying an implant for example, burden onto a patient is relatively small, safety of the patient is quite good and also the safety of the operator is rather high.

When using the puncture apparatus for treating a woman's urinary incontinence, for example, the urethral-insertion member of aforesaid puncture apparatus is inserted into her urethra, the puncture needle is moved rotationally, and her living body is punctured by the puncture needle. At that time, the needle tip of the puncture needle passes a far-position side from the center of the puncture needle compared with the urethral-insertion member, so that it is possible to puncture the living body by avoiding the urethra and it is possible to prevent a phenomenon that the puncture needle is to puncture the urethra. Also, it is possible to prevent a phenomenon that the finger tip of the operator is punctured by the puncture needle.

Also, when burying an implant for treatment of the urinary incontinence, incision of a vagina wall is not necessary and it is possible to bury that implant by a relatively low invasive procedure. Also, it is possible to prevent a phenomenon in which, such as in a case of incising a vagina, the implant will be exposed to the inside of the vagina from a wound caused by the incision and in which there occur complications which are to be caused by an infection from the wound or the like, and it is very safe and it is possible to bury the implant reliably.

Also, similar benefits can be realized for disorders in which a position deviation of an organ occurs in the inside of the living body such as a case of a pelvic floor disorder or the like.

The puncture apparatus and method here thus exhibit industrial usability.

Figure 28:
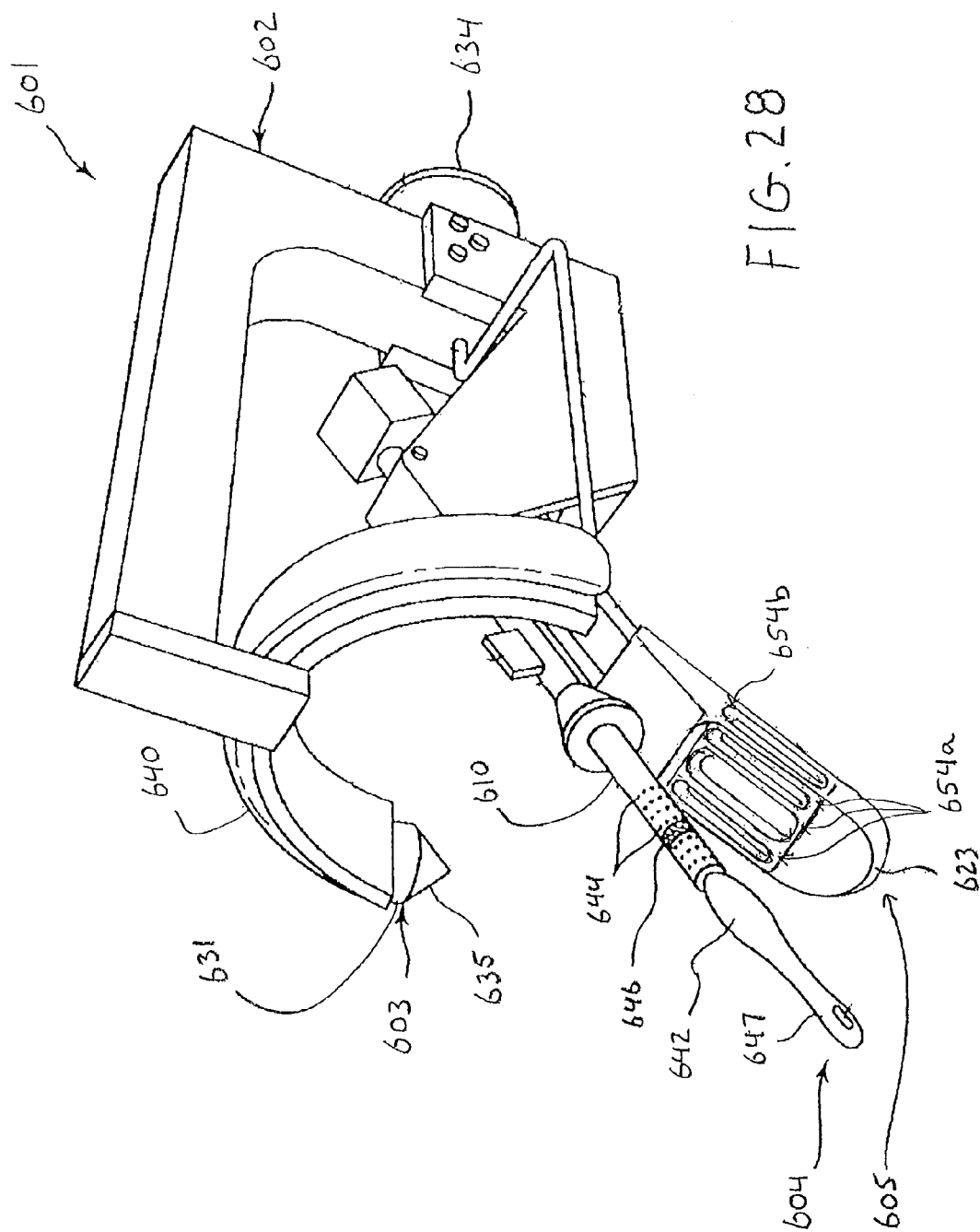
FIG. 28 is a perspective view of another embodiment of the puncture apparatus.
Figure 29:
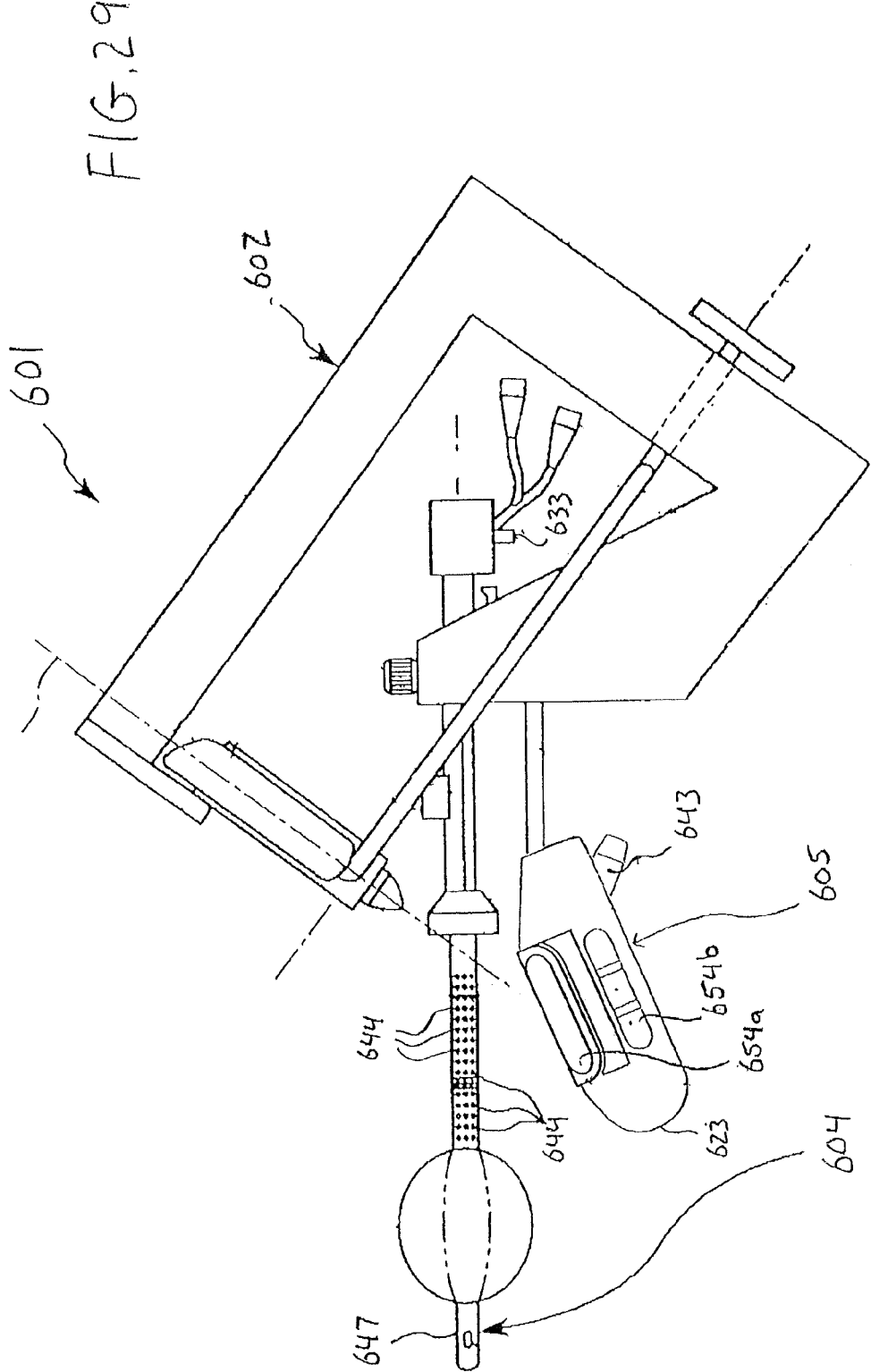
FIG. 29 is a side view of the puncture apparatus shown in FIG. 28.

FIGS. 28 and 29 illustrate another different embodiment of the puncture apparatus. Details and aspects of this embodiment of the puncture apparatus that are the same as or similar to those described above in connection with the other embodiments are not be described again in detail here.

The puncture apparatus 601 shown in FIGS. 28 and 29 includes a supporting member 602, a puncture member 603, a urethral-insertion member 604 and a vaginal-insertion member 605. The urethral-insertion member 604 and the vaginal-insertion member 605 are both supported on, or mounted on, the supporting member 602. The puncture member 603 includes a puncture needle 631 possessing a sharp needle tip 635. In this embodiment, the puncture member 603 is movably positioned within a needle guide 640. The puncture member 603 moves along the predetermined orbit as described above through operation of the grasping unit or operating unit 634. That is, the grasping unit or operating unit 634 is operatively connected to the puncture member 603 so that operation of the grasping unit or operating unit 634 causes the puncture member 603 to rotate about its rotation axis and move along the predetermined orbit as described above.

The urethral-insertion member 604 is sized and configured to be inserted into and positioned in the urethra. The urethral-insertion member 604 includes an elongated tubular member 610 in which is movably positioned a balloon catheter having an inflatable balloon 642 at its distal end. The balloon 642 is similar to the balloon 111 described above. The urethral-insertion member 604 also includes a marker 641 similar to the marker 41 described above.

In this embodiment of the puncture apparatus, the urethral-insertion member 604 and the vaginal-insertion member 605 are configured to include vacuum areas or suction areas that draw a portion of the urethra wall and vaginal wall toward, and preferably into direct contact with, the outer surface of the urethral-insertion member 604 and the vaginal-insertion member 605 respectively. The tubular member 610, forming a part of the urethral-insertion member 604, includes a plurality of openings or open areas 44 passing through the tubular member 610 and communicating with the interior of the tubular member 610. The openings or open areas 44 define the vacuum area or suction area of the urethral-insertion member 604. The interior of the tubular member 610 communicates with a suction port 633 that is configured to be connected to a source of suction. As will be described in more detail below, the source of suction is operated when the urethral-insertion member 604 is positioned in the urethra, and this creates a vacuum (suction) in the vacuum area defined by the openings or open areas 644. The vacuum or suction draws the wall of the urethra towards, and preferably into direct contact with, the outer surface of the ureteral-insertion member 604.

The vaginal-insertion member 605 is sized and configured to be inserted into and positioned in the vagina. The vaginal-insertion member 605 is a generally elongated member, having a somewhat rounded forward end 623. The top surface of the vaginal-insertion member 605 includes a vacuum area (suction area) defined by a plurality of openings or open areas 654*a*, and both side surfaces of the vaginal-insertion member 605 include respective vacuum areas (suction areas) defined by a plurality of openings or open areas 654*b*. The openings or open areas 654*a*, 654*b* are in fluid communication with a suction port 643 which is connectable to a source of suction. As will be described in more detail below, the source of suction is operated when the vaginal-insertion member 605 is positioned in the vagina, and this creates a vacuum (suction) in the vacuum areas defined by the openings or open areas 654*a*, 654*b*. The vacuum or suction created at the vacuum area defined by the openings or open areas 654 draws the vaginal wall towards, preferably into direct contact with, the outer surface of the vaginal-insertion member 605.

The operating procedure using the puncture apparatus 601 is similar to the procedure described above. Initially, the puncture apparatus 601 is attached to or mounted on the patient. This involves inserting the urethral-insertion member 604 into the urethra of the living body (patient), and concurrently inserting the vaginal-insertion member 605 into the vagina of the living body (patient). The insertion of the urethral-insertion member 604 is preferably carried out to position the marker 646 at the urethra orifice or on the front side of the urethra orifice so that the distal portion of the urethral-insertion member 604 is arranged on the front side of the bladder.

Next, the source(s) of suction connected to the suction ports 633, 643 of the urethral-insertion member 604 and the vaginal-insertion member 605 is operated to create a vacuum (produce a suction force) at the vacuum areas defined by the openings or open areas 644, 654*a*, 654*b* of the vaginal-insertion member 605 and the ureteral-insertion member 604. This vacuum force draws the vaginal wall toward the vaginal-insertion member 605 and draws the urethra wall towards the urethral-insertion member 604. The operation of the suction source(s) fixes the position of the vagina and the urethra, allowing the needle to be operated to create the through-hole between the vaginal-insertion member 605 and the urethral-insertion member 604.

During the operation of the suction source(s) (i.e., while the vacuum or suction force is being produced at the vacuum areas defined by the openings or open areas 644), the puncture needle is rotated through operation of the grasping unit 634. The needle tip thus punctures skin of the living body (patient) so that the puncture member 603 enters the body. Continued rotation of the puncture member causes the puncture member to pass the obturator foramen of the pelvis, then to pass between the urethra and the vagina, and then to pass the obturator foramen of the pelvis, and finally to exit or protrudes to outside the body in a manner similar to that described above. A through-hole is thus formed which starts from the surface of the living body (patient), passes through a portion of the body as described and reaches the body surface at a region spaced from the start region. The through hole, passing between the vaginal-insertion member 605 and the urethral-insertion member 604, provides a path for placing the implant or sling. Throughout the rotation or operation of the puncture needle, the suction source(s) connected to the suction ports 633, 643 of the urethral-insertion member 604 and the vaginal-insertion member 605 continues to be operated so that the vacuum force draws the vaginal wall toward the vaginal-insertion member 605 and draws the urethra wall towards the urethral-insertion member 604.

The embodiment of the puncture apparatus shown in FIGS. 28 and 29 includes the vaginal-insertion member 605 provided with openings or open areas 654 defining a vacuum area. To help avoid the these openings or open areas 654 defining the vacuum areas from presenting the possibility for damaging the vaginal wall during insertion of the vaginal-insertion member into the vagina, FIGS. 30-32 illustrate a vaginal-insertion assembly 1605 that can be used in place of, or as a specific form of, the vaginal-insertion member 605 in the puncture apparatus illustrated in FIGS. 28 and 29. The vaginal-insertion assembly 1605 can also be used together with any of the other embodiments of the puncture apparatus described above and illustrated in the drawing figures.

The vaginal-insertion assembly 1605 includes the vaginal-insertion member 1610, similar to the vaginal-insertion member 605 shown in FIGS. 28 and 29, together with a cover 1630. The cover 1630 encircles or surrounds the outer surface of the vaginal-insertion member 1610. More specifically, the cover is preferably configured to overlie or cover the entirety of the openings or open areas 654a, 654b on the top and the sides of the vaginal-insertion member 1610 that form the vacuum areas (suction areas). The cover 1630 thus has a longitudinal or axial extent at least as long as the longitudinal or axial extent of the openings or open areas 654a, 654b so that the cover is able to completely cover the openings or open areas 654a, 654b. In the illustrated embodiment, the cover 1630 possesses a longitudinal or axial extent that is slightly less than the overall longitudinal or axial extent of the vaginal-insertion member 1610. The cover 1630 extends around the entire circumferential extent of the vaginal-insertion member 1610.

The cover 1630 includes a relatively narrow and longitudinally extending slit 1632 as shown in FIG. 31. In the illustrated embodiment, the slit 1632 extends along the entire longitudinal or axial extent of the cover 1630 so that the slit 1632 is open at both ends. The slit 1632 is positioned on the surface of the vaginal-insertion member 1610 at which is located the suction port 1643 that is connected to the suction source. The suction port 1643 corresponds to the suction port 643 shown in FIGS. 28 and 29, and described above. Thus, in this embodiment, the slit 1632 is positioned on the bottom surface of the vaginal-insertion member 1610.

As shown in FIGS. 30-32, the cover 1630 is provided with a handle or tab 1635 projecting away from the remainder of the cover and configured to be grasped or held by the user. The handle or tab 1635 allows the user to move or slide the cover 1630 in the proximal direction (to the right in FIGS. 30-32) relative to the vaginal-insertion member 1610 to expose the vacuum areas (openings or open areas 654a, 654b) once the vaginal-insertion member 1610 has been properly positioned in the vagina. The slit 1632 allows the cover to move past the suction port 643 when the user slides the cover 1630 relative to the vaginal-insertion member 1610. That is, when the handle 1635 is pulled in the proximal direction (i.e., to the right in FIGS. 30-32), the cover 1630 slides relative to the vaginal-insertion member and moves past the suction port 643 by virtue of the presence of the slit 1632. The slit 1632 widens as the cover moves past the suction port 643.

In use, the vaginal-insertion assembly (i.e., the vaginal-insertion member 1610 and the cover 1630) is inserted into the vagina by way of the vaginal opening to properly position the vaginal-insertion member 1610 in the vagina. During this insertion of the vaginal-insertion assembly 1605, the cover 1630 is positioned in covering relation to the openings or open areas 654a, 654b so that the openings or open areas 654a, 654b are not exposed. The vaginal-insertion assembly 1605 can thus be inserted into the vagina without concern that the openings or open areas 654a, 654b will contact and possibly damage the vaginal wall. After the vaginal-insertion assembly 1605 is properly positioned in the vagina, the user pulls the handles or tabs 1635 in the proximal direction to slide the cover 1630 relative to the vaginal-insertion member 1610 to thus completely remove the cover 1630 from the vaginal-insertion member 1610. The vacuum areas defined by the openings or open areas 654a, 654b on the vaginal-insertion member 1610 are thus exposed. The operation described above, in which the vacuum areas draw the vaginal wall toward the vaginal-insertion member 1610, can then be performed.

FIGS. 33 and 34 illustrate an alternative embodiment of the vaginal-insertion assembly 1705 utilizing a modified version of the cover 1730.

This embodiment of the vaginal-insertion assembly 1705 includes a cover 1730 slidably mounted on the vaginal-insertion member 1710. In this embodiment, the cover 1730 includes projecting portions 1732 on opposites sides of the cover 1730 that are positioned in and slide along rails or grooves 1715 extending longitudinally along opposite sides of the vaginal-insertion member 1710. The cover 1730 is sized to cover all of the openings or open areas 654a, 654b on the top and the sides of the vaginal-insertion member 1710. In the position illustrated in FIG. 33, the cover 1730 covers the top and sides of the vaginal-insertion member 1710. The cover 1730 thus has a longitudinal or axial extent at least as long as the longitudinal or axial extent of the openings or open areas in the vaginal-insertion member 1710 (the openings or open areas 654a, 654b) so that the cover 1730 is able to completely cover the openings or open areas. In the illustrated embodiment, the cover 1730 possesses a longitudinal or axial extent that is slightly less than the overall longitudinal or axial extent of the vaginal-insertion member 1710.

The cover 1730 is provided with a handle or tab 1735 similar to the handle or tab 1635 described above. This handle or tab 1735 projects away from the remainder of the cover 1730 and is configured to be grasped or held by the user. The handle or tab 1735 can be held or grasped by the user to move or slide the cover 1730 in the proximal direction (to the right in FIG. 33) relative to the vaginal-insertion member 1710 to expose the vacuum areas (openings or open areas 654a, 654b), after the vaginal-insertion member 1710 is properly positioned in the vagina.

The use of the vaginal-insertion assembly 1705 is similar to that described above with respect to the vaginal-insertion assembly 1605. That is, the vaginal-insertion assembly 1705 is inserted into the vagina by way of the vaginal opening to properly position the vaginal-insertion member 1710 in the vagina. As the vaginal-insertion assembly 1705 is being inserted into the vagina, the cover 1730 is positioned to cover all of the openings or open areas on the vaginal-insertion member 1710 (i.e., the openings or open areas like the openings or open areas 654a, 654b shown in FIGS. 28 and 29) so that the openings or open areas are not exposed. The vaginal-insertion assembly 1705 can thus be inserted into the vagina without concern that the openings or open areas will contact and possibly damage the vaginal wall. After the vaginal-insertion assembly 1705 is positioned in the vagina at the desired location, the user pulls the handles or tabs 1735 in the proximal direction to slide the cover 1730 relative to the vaginal-insertion member 1710. The vacuum areas defined by the openings or open areas on the vaginal-insertion member 1710 are thus exposed. The vaginal-insertion assembly 1705 can be configured so that the cover 1730 is completely removed from the vaginal-insertion member 1710. This can be accomplished by configuring the grooves or rails 1715 such that the proximal ends of the grooves or rails 1715 taper in depth to approach the outer surface of the vaginal-insertion member 1710. The operation described above, in which the vacuum areas draw the vaginal wall toward the vaginal-insertion member 1710, can then be performed.

Figure 35:
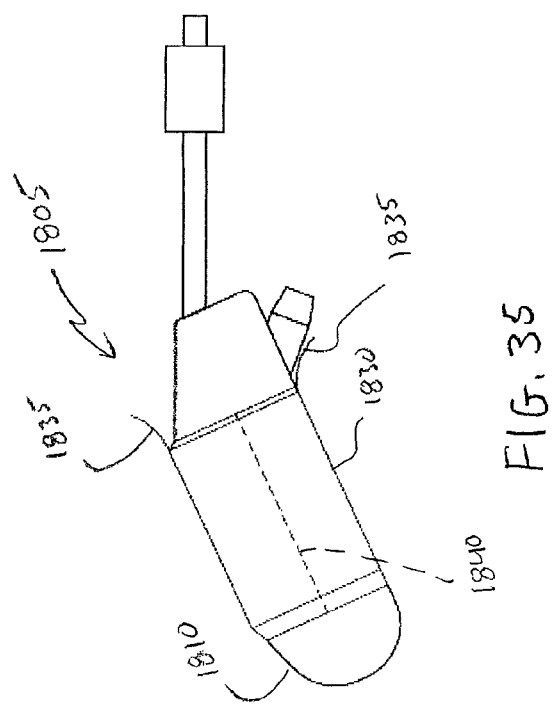
FIG. 35 is a side view of a vaginal-insertion assembly according to another embodiment disclosed here by way of example.
Figure 37:
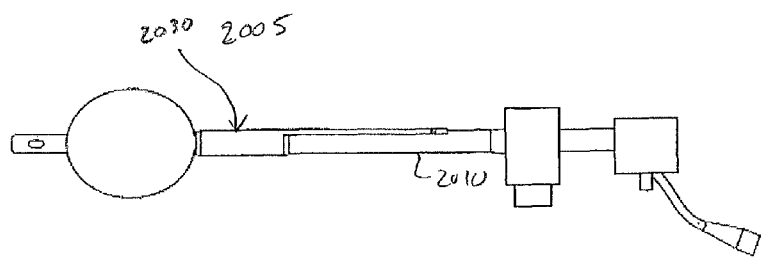
FIG. 37 is a side view of a uretheral-insertion assembly that includes a cover which covers the vacuum area(s).
Figure 38:
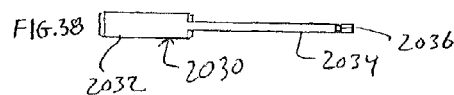
FIG. 38 is a plan view of the cover.

FIG. 35 illustrates another embodiment of the vaginal-insertion assembly 1605 utilizing a different cover 1830. In this version, the cover 1830 that is mounted on the vaginal-insertion member 1810 is provided with a splittable or separable portion(s) 1840. The illustrated version shows a splittable or separable portion 1840 extending longitudinally along one side of the cover, but it is understood that there is another splittable or separable portion at a position circumferentially spaced apart from the illustrated splittable or separable portion 1840. For example, the other splittable or separable portion could be positioned diametrically opposite the illustrated splittable or separable portion(s) 1840. In the illustrated embodiment, the splittable or separable portion 1840 extends longitudinally along the entire longitudinal or axial extent of the cover 1830. This splittable or separable portion 1840 can be in the form of one or more longitudinally extending weakening lines (e.g., perforations) in the material forming the cover 1830.

The cover 1830 is preferably configured to overlie or cover the entirety of the openings or open areas (opening or open areas like the opening or open areas 654a, 654b shown in FIGS. 28 and 29) on the top and the sides of the vaginal-insertion member 1810 that form the vacuum areas (suction areas). The cover 1830 in this embodiment encircles or surrounds the entire circumferential extent of the outer surface of the vaginal-insertion member 1810. The longitudinal or axial extent of the cover 1630 is at least as long as the longitudinal or axial extent of the openings or open areas on the vaginal-insertion member 1810 so that the cover 1830 is able to completely cover the openings or open areas. Like in the earlier embodiments, the cover possesses a longitudinal or axial extent that is slightly less than the overall longitudinal or axial extent of the vaginal-insertion member 1810. The cover 1830 also include handles or tabs 1835 which can be held and pulled by the user to split the cover 1830 along the separable or splittable portion(s) 1840 to thus allow the cover to be separated and removed from the vaginal-insertion member 1810.

The use of the vaginal-insertion assembly 1805 is similar to that described above with respect to the vaginal-insertion assemblies 1605, 1705. The vaginal-insertion assembly 1805 is inserted into the vagina by way of the vaginal opening to properly position the vaginal-insertion member 1810 in the vagina. As the vaginal-insertion assembly 1805 is being inserted into the vagina, the cover 1830 is positioned in covering relation to all of the openings or open areas on the vaginal-insertion member 1810 (i.e., the openings or open areas like the openings or open areas 654a, 654b shown in FIGS. 28 and 29) so that the openings or open areas are not exposed. It is thus possible to insert the vaginal-insertion assembly 1805 into the vagina without damaging the vaginal wall through contact of the openings or open areas with the vaginal wall. After the vaginal-insertion assembly 1805 is positioned in the vagina at the desired location, the user can pull the handles or tabs 1835 in the proximal direction to split or separate the cover 1830 in a manner which allows the cover 1830 to be removed from the vaginal-insertion member 1810. This thus exposes the openings or open areas on the vaginal-insertion member 1810 forming the vacuum areas or suction areas.

Figure 36:
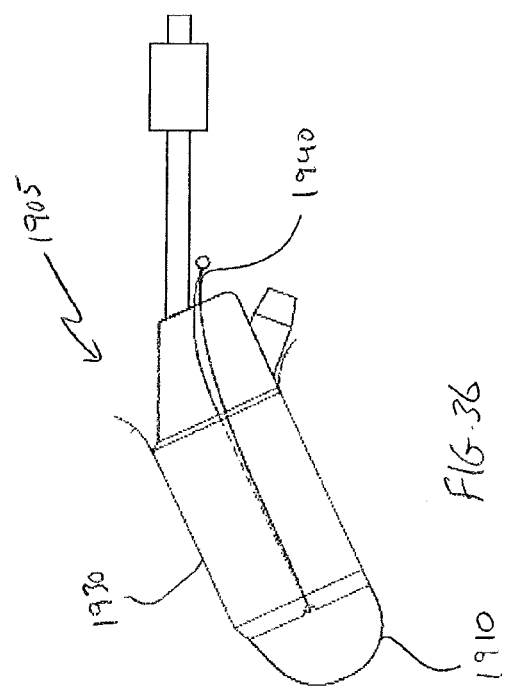
FIG. 36 illustrates another embodiment of the vaginal-insertion assembly disclosed by way of example.

FIG. 36 illustrates another embodiment of the vaginal-insertion assembly 1905 comprised of the vaginal-insertion member 1910 and a cover 1930. The cover 1930 used in this embodiment of the vaginal-insertion assembly is the same as the cover shown in FIG. 35 and described above, except that the cover 1930 according to this embodiment additionally includes at least one pull strip 1940 that is fixed to the cover 1930. By pulling on the pull strip 1940, it is possible to separate the cover 1930 so that the cover 1930 can be removed from the vaginal-insertion member after the vaginal-insertion assembly 1905 is positioned in the vagina.

Other features and aspects of the cover 1930 are the same as described above with respect to the cover 1830 and so a detailed description of such features and aspects is not repeated here. The use of the vaginal-insertion assembly 1905 having the cover 1930 is also the same as described above with respect to the vaginal-insertion assembly 1805 with the cover 1830, except that separating the cover 1930 from the vaginal-insertion member 1910 is accomplished by pulling on the pull strip 1940.

The description above, and the illustrations in FIGS. 30-36, describes various embodiments of a vaginal-insertion assembly outfitted with a cover to inhibit or prevent damage to the vaginal wall. The cover functions to cover and prevent exposure of the openings or open areas on the vaginal-insertion member that define vacuum or suction areas so that such openings or open areas are not liable to contact the vaginal wall. The description above about the puncture apparatus shown in FIGS. 28 and 29 explains that not only does the vaginal-insertion member include openings or open areas, but so too does the uretheral-insertion member. To inhibit or prevent damage to the uretheral wall during insertion of the uretheral-insertion member into the urethra, the uretheral-insertion member is preferably also provided with a cover.

FIGS. 37-40 illustrate a cover having useful application to the uretheral-insertion member 604 shown in FIGS. 28 and 29. The cover 2030 and the uretheral-insertion member 2010 together form a uretheral-insertion assembly 2005. The cover 2030 is slidably mounted on the uretheral-insertion member 2010. The cover 2030 includes a tubular member 2032 at the distal end of the cover 2030, and an extension 2034 at the proximal end of the cover 2030. In this embodiment disclosed by way of example, the tubular member 2032 and the extension 2034 are integrally formed in a unitary manner in one-piece at the same time.

The tubular member 2032 extends around the entire circumferential extent of the uretheral-insertion member 2010 to cover all of the openings or open areas 2044 in the uretheral-insertion member 2010 forming the vacuum area (s). The cover 2030 is thus sized to cover all of the openings or open areas 2044 of the uretheral-insertion member 2010. The cover 2030 thus has a longitudinal or axial extent at least as long as the longitudinal or axial extent of the openings or open areas 2044 in the uretheral-insertion member 2010 so that the cover 2030 is able to completely cover all of the openings or open areas.

Figure 39:
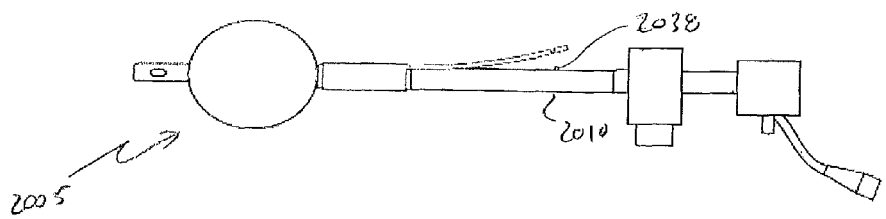
FIG. 39 is a side view of the uretheral-insertion assembly in which the cover is disengaged from the stopper.
Figure 40:
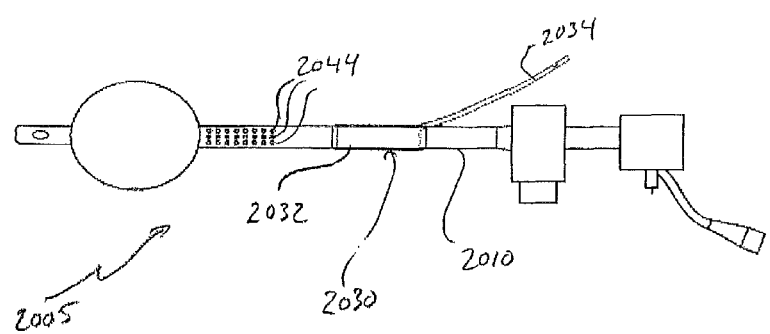
FIG. 40 is a side view of the uretheral-insertion assembly with the cover moved rearwardly to expose the openings forming the vacuum area(s).

The extension 2034 is fixed to the tubular member 2032 and axially extends or projects in the proximal direction away from the tubular member 2032. The extension 2034 includes a hole 2036 configured to receive a projection 2038 projecting away from the uretheral-insertion member 2010. The hole 2036 and the projection 2038 together form a stopper that prevents the cover 2030 from sliding relative to the uretheral-insertion member. That is, when the projection 2038 is positioned in the hole 2036 in the extension 2034 of the cover 2030, the cover 2030 is positionally fixed relative to the uretheral-insertion member 2010. On the other hand, as illustrated in FIG. 39, the free end of the extension 2034 can be lifted away from the uretheral-insertion member 2010 to disengage the extension 2034 from the projection 2038 and thus allow the cover 2030 to slide rearwardly in the proximal direction (i.e., to the right in FIGS. 39 and 40) relative to the uretheral-insertion member 2010, thus allowing the openings 2044 in the uretheral-insertion member to be exposed. The vacuum or suction area(s) of the uretheral-insertion member is thus exposed. Once the vacuum or suction area(s) is exposed, the suction source can be operated to draw the uretheral wall toward the uretheral-insertion member 2010 as described above in connection with the description of the puncture apparatus shown in FIGS. 28 and 29.

In use the uretheral-insertion assembly 2005 is inserted into the urethra. At this time, the cover 2030 is positioned in the manner shown in FIG. 37 so that the openings or open areas 2044 forming the vacuum or suction area(s) are covered. When the uretheral-insertion assembly 2005 is inserted into urethra, the openings 2044 are thus not exposed and not liable to cause damage to the uretheral wall. After the uretheral-insertion assembly has been inserted into the urethra and positioned at the desired location, the free end of the extension 2034 is lifted to disengage the hole 2036 from the projection 2038 so that the stopper is disengaged or released. The extension 2034 is then rearwardly pulled in the proximal direction to likewise move the tubular member 2032 in the rearward direction to expose the openings 2044 so that the vacuum or suction area(s) is exposed.

Having described, by way of example, embodiments of the puncture apparatus and method, it is to be understood that the invention here is not limited to those precise embodiments and that various changes and modifications could be effected therein by one skilled in the art without departing from the spirit or scope of the invention as defined in the claims.

What is claimed is:

1. A puncture apparatus comprising:
   a supporting member;
   a puncture member rotatably mounted on the supporting member to rotate about a rotation center, the puncture member possessing a distal end portion, at least a portion of the rotatable puncture member being bent or curved, the distal end portion of the puncture member constituting a needle tip which rotates together with the puncture member and is configured to puncture living body tissue as the puncture member is rotated about the rotation center;
   a vaginal-insertion member mounted on the supporting member and insertable into a vagina of a living body;
   a urethra insertion member mounted on the supporting member and insertable into a urethra of the living body;
   at least one of the vaginal-insertion member and the urethra insertion member including a vacuum area connected to a suction port which is configured to be communicated with a suction source to create a vacuum in the vacuum area;
   a cover covering the vacuum area so that the vacuum area does not contact and damage a wall of the living body; and
   the cover being movable relative to the vacuum area to expose the vacuum area.

2. The puncture apparatus according to claim 1, wherein the vacuum area is provided on the vaginal-insertion member, and the cover covers the vacuum area on the vaginal-insertion member.

3. The puncture apparatus according to claim 1, wherein the vacuum area is provided on the urethra insertion member, and the cover covers the vacuum area on the urethra insertion member.

4. The puncture apparatus according to claim 1, wherein the cover includes a slit extending along a longitudinal extent of the cover, the suction port moving along the slit as the cover moves relative to the vacuum area.

5. The puncture apparatus according to claim 1, wherein the vacuum area is provided on the vaginal-insertion member, and the cover covers the vacuum area on the vaginal-insertion member, the cover including rails on opposite sides of the cover that slide in respective slots on opposite sides of the vaginal-insertion member.

6. The puncture apparatus according to claim 1, wherein the cover includes a splittable portion at which the cover is separable along a longitudinal extent of the cover to permit removal of the cover.

7. The puncture apparatus according to claim 1, wherein the vacuum area is provided on the vaginal-insertion member, and the cover includes a pull strip that longitudinally splits the cover portion when the pill strip is pulled to separate the cover along a longitudinal extent of the cover to permit removal of the cover from the vaginal-insertion member.

8. The puncture apparatus according to claim 1, wherein the vacuum area is provided on the urethra insertion member, and the cover covers the vacuum area on the urethra insertion member and is slidable along a longitudinal extent of the urethra insertion member.

9. The puncture apparatus according to claim 1, wherein the vacuum area is provided on the urethra insertion member, and the cover is a tubular member that circumferentially encircles the urethra insertion member.

10. The puncture apparatus according to claim 1, wherein the vacuum area is provided on the urethra insertion member, and the cover covers the vacuum area on the urethra insertion member, and the urethra insertion member includes a stopper that engages the cover to positionally fix the cover on the urethra insertion member and prevent the cover from moving along the urethra insertion member.

11. A living body insertion assembly comprising:
    a supporting member;
    a puncture member rotatably mounted on the supporting member to rotate about a rotation center, the puncture member possessing an end portion configured to puncture living body tissue;
    an insertion member mounted on the supporting member and configured and sized to be inserted into a part of a living body, the part of the living body being one of a vagina and a urethra;
    the insertion member including a vacuum area connected to a suction port which is configured to be communicated with a suction source to create a vacuum in the vacuum area of the insertion member to draw a wall of the part of the living body toward the vacuum area when the insertion member is positioned in the part of the living body;

a cover covering the vacuum area so that the vacuum area does not contact and damage the wall of the part of the living body when the insertion member is inserted into the part of the living body; and the cover being movable relative to the insertion member to expose the vacuum area after the insertion member is positioned in the part of the living body.

12. The living body insertion assembly according to claim 11, wherein the cover includes a slit extending along a longitudinal extent of the cover, the suction port moving along the slit when the cover is moved relative to the insertion member to expose the vacuum area.

13. The living body insertion assembly according to claim 11, wherein the cover includes rails on opposite sides of the cover that slide in respective slots on opposite sides of the insertion member.

14. The living body insertion assembly according to claim 11, wherein the cover includes a splittable portion at which the cover is separable along a longitudinal extent of the cover to permit removal of the cover from the insertion member.

15. The living body insertion assembly according to claim 11, wherein the cover includes a pull strip that longitudinally splits the cover portion when the pull strip is pulled to separate the cover along a longitudinal extent of the cover to permit removal of the cover from the insertion member.

* * * * *